(12) United States Patent
Fukuda et al.

(10) Patent No.: US 10,259,844 B2
(45) Date of Patent: *Apr. 16, 2019

(54) ENDOMETRIOSIS CELL TARGETING PEPTIDE AND USES THEREOF

(71) Applicants: Sanford-Burnham Medical Research Institute, LaJolla, CA (US); Keio University, Tokyo (JP); Noriko Nozawa

(72) Inventors: Michiko Fukuda, LaJolla, CA (US); Daisuke Aoki, Shinjuku-ku (JP); Shiro Nozawa, Shibuya-ku (JP)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 229 days.

This patent is subject to a terminal disclaimer.

(21) Appl. No.: 14/683,520

(22) Filed: Apr. 10, 2015

(65) Prior Publication Data

US 2015/0353603 A1    Dec. 10, 2015

Related U.S. Application Data

(62) Division of application No. 11/616,098, filed on Dec. 26, 2006, now Pat. No. 9,006,404.

(60) Provisional application No. 60/753,677, filed on Dec. 23, 2005.

(51) Int. Cl.

| A61K 38/00 | (2006.01) |
| C07K 7/08 | (2006.01) |
| A61K 49/00 | (2006.01) |
| A61K 31/7028 | (2006.01) |
| A61K 45/06 | (2006.01) |
| G01N 33/569 | (2006.01) |
| A61K 38/08 | (2019.01) |
| C07K 7/06 | (2006.01) |
| C07K 14/00 | (2006.01) |
| A61K 47/64 | (2017.01) |

(52) U.S. Cl.
CPC ............ *C07K 7/08* (2013.01); *A61K 31/7028* (2013.01); *A61K 38/08* (2013.01); *A61K 45/06* (2013.01); *A61K 47/64* (2017.08); *A61K 49/0056* (2013.01); *C07K 7/06* (2013.01); *C07K 14/001* (2013.01); *G01N 33/56966* (2013.01); *G01N 2800/364* (2013.01)

(58) Field of Classification Search
None
See application file for complete search history.

(56) References Cited

U.S. PATENT DOCUMENTS

| 6,540,980 B1 * | 4/2003 | Blumenthal | A61K 47/48646 424/1.11 |
| 2002/0064823 A1 * | 5/2002 | Welcher | C07K 14/705 435/69.1 |
| 2004/0001823 A1 * | 1/2004 | Yeaman | G01N 33/564 424/130.1 |

FOREIGN PATENT DOCUMENTS

WO       WO 0067771 A1 * 11/2000 ............. C07K 14/78

OTHER PUBLICATIONS

Printout of https://www.ncbi.nlm.nih.gov/protein/q9z5a2 retrieved Mar. 30, 2017.*
Crosignani P, Olive D, Bergqvist A, Luciano A, Advances in the management of endometriosis: an update for clinicians. Hum Reprod Update. Mar.-Apr. 2006;12(2):179-89. Epub Nov. 9, 2005.
Schally AV, Nagy A. Chemotherapy targeted to cancers through tumoral hormone receptors. Trends Endocrinol Metab. Sep. 2004;15(7):300-10.
UniProt accession No. Q7YLR6 "Small ribosomal protein 4 (fragment)" Oct. 25, 2005.
Aoki, D., Katsuki, Y., Shimizu, A., Kakinuma, C. & Nozawa, S. (1994) Successful heterotransplantation of human endometrium in SCID mice. Obstet Gynecol 83, 220-8.
Arap, W., Pasqualini, R. & Ruoslahti, E. (1998) Cancer treatment by targeted drug delivery to tumor vasculature in a mouse model. Science 279, 377-80.
Arici, A., Matalliotakis, I., Goumenou, A., Koumantakis, G., Fragouli, Y. & Mahutte, N. G. (2003) Increased pregnancy-associated plasma protein-A (PAPP-A) concentrations in peritoneal fluid of women with endometriosis. Am J Reprod Immunol 49, 70-4.
Arimoto, T., Katagiri, T., Oda, K., Tsunoda, T., Yasugi, T., Osuga, Y., Yoshikawa, H., Nishii, O., Yano, T., Taketani, Y. & Nakamura, Y. (2003) Genome-wide cDNA microarray analysis of gene-expression profiles involved in ovarian endometriosis. Int J Oncol 22, 551-60.
Awwad, J. T., Sayegh, R. A., Tao, X. J., Hassan, T., Awwad, S. T. & Isaacson, K. (1999) The SCID mouse: an experimental model for endometriosis. Hum Reprod 14, 3107-11.
Barbieri, R. L. & Missmer, S. (2002) Endometriosis and infertility: a cause-effect relationship? Ann N Y Acad Sci 955, 23-33.
Barbieri, R. L. (1988) New therapy for endometriosis. N Engl J Med 318, 512-4.
Castelbaum, A. J., Ying, L., Somkuti, S. G., Sun, J., Ilesanmi, A. O. & Lessey, B. A. (1997) Characterization of integrin expression in a well differentiated endometrial adenocarcinoma cell line (Ishikawa). J Clin Endocrinol Metab 82, 136-42.
Cramer, D. W. & Missmer, S. A. (2002) The epidemiology of endometriosis. Ann N Y Acad Sci 955, 11-22.
De Maria, R., Lenti, L., Malisan, F., d'Agostino, F., Tomassini, B., Zeuner, A., Rippo, M. R., and Testi, R. Requirement for GD3 ganglioside in CD95- and ceramide-induced apoptosis. Science, 277: 1652-1655, 1997.

(Continued)

*Primary Examiner* — Michael Szperka
(74) *Attorney, Agent, or Firm* — Pabst Patent Group LLP

(57) ABSTRACT

Provided herein are compositions and methods for selectively targeting an endometriosis cell.

31 Claims, 6 Drawing Sheets

Specification includes a Sequence Listing.

(56) References Cited

OTHER PUBLICATIONS

Desai, N. N., Kennard, E. A., Kniss, D. A. & Friedman, C. I. (1994) Novel human endometrial cell line promotes blastocyst development. Fertil Steril 61, 760-6.
Ellerby, H. M., Arap, W., Ellerby, L. M., Kain, R., Andrusiak, R., Rio, G. D., Krajewski, S., Lombardo, C. R., Rao, R., Ruoslahti, E., Bredesen, D. E. & Pasqualini, R. (1999) Anti-cancer activity of targeted pro-apoptotic peptides. Nat Med 5, 1032-8.
Essler, M. & Ruoslahti, E. (2002) Molecular specialization of breast vasculature: a breast-homing phage-displayed peptide binds to aminopeptidase P in breast vasculature. Proc Natl Acad Sci U S A 99, 2252-7.
Eyster, K. M., Boles, A. L., Brannian, J. D. & Hansen, K. A. (2002) DNA microarray analysis of gene expression markers of endometriosis. Fertil Steril 77, 38-42.
Fukuda, M. N., Sato, T., Nakayama, J., Klier, G., Mikami, M., Aoki, D. & Nozawa, S. (1995) Trophinin and tastin, a novel cell adhesion molecule complex with potential involvement in embryo implantation. Genes Dev 9, 1199-210.
Fukuda MN, Ohyama C, Lowitz K, Matsuo O, Pasqualini R, Ruoslahti E, Fukuda M. A peptide mimic of E-selectin ligand inhibits sialyl Lewis X-dependent lung colonization of turmor cells.Cancer Res. Jan. 15, 2000;60(2):450-6.
Gerlag, D. M., Borges, E., Tak, P. P., Ellerby, H. M., Bredesen, D. E., Pasqualini, R., Ruosiahti, E. & Firestein, G. S. (2001) Suppression of murine collagen-induced arthritis by targeted apoptosis of synovial neovasculature. Arthritis Res 3, 357-61.
Gong, Y., Murphy, L. C. & Murphy, L. J. (1994) Hormonal regulation of proliferation and transforming growth factors gene expression in human endometrial adenocarcinoma xenografts. J Steroid Biochem Mol Biol 50, 13-9.
Grummer, R., Schwarzer, F., Bainczyk, K., Hess-Stumpp, H., Regidor, P. A., Schindler, A. E. & Winterhager, E. (2001) Peritoneal endometriosis: validation of an in-vivo model. Hum Reprod 16, 1736-43.
Haffner, M. E., Whitley, J. & Moses, M. (2002) Two decades of orphan product development. Nat Rev Drug Discov 1, 821-5.
Kao, L. C., Germeyer, A., Tulac, S., Lobo, S., Yang, J. P., Taylor, R. N., Osteen, K., Lessey, B. A. & Giudice, L. C. (2003) Expression profiling of endometrium from women with endometriosis reveals candidate genes for disease-based implantation failure and infertility. Endocrinology 144, 2870-81.
Kolonin, M. G., Saha, P. K., Chan, L., Pasqualini, R. & Arap, W. (2004) Reversal of obesity by targeted ablation of adipose tissue. Nat Med 10, 625-32.
Lessey, B. A., Damjanovich, L., Coutifaris, C., Castelbaum, A., Albelda, S. M. & Buck, C. A. (1992) Integrin adhesion molecules in the human endometrium. Correlation with the normal and abnormal menstrual cycle. J.Clin.Invest. 90, 188-195.
Lessey, B. A., Ilesanmi, A. O., Castelbaum, A. J., Yuan, L., Somkuti, S. G., Chwalisz, K. & Satyaswaroop, P. G. (1996) Characterization of the functional progesterone receptor in an endometrial adenocarcinoma cell line (Ishikawa): progesterone-induced expression of the alpha1 integrin. J Steroid Biochem Mol Biol 59, 31-9.
Malisan, F., and Testi, R. GD3 ganglioside and apoptosis. GD3 ganglioside and apoptosis. Biochim Biophys Acta, 1585: 179-187, 2002.
Matsuzaki, S., Canic, M., Vaurs-Barriere, C., Pouly, J. L., Boespflug-Tanguy, O., Penault-Llorca, F., Dechelotte, P., Dastugue, B., Okamura, K. & Mage, G. (2004) DNA microarray analysis of gene expression profiles in deep endometriosis using laser capture microdissection. Mol Hum Reprod 10, 719-28.
Murphy, A. A. (2002) Clinical aspects of endometriosis. Ann N Y Acad Sci 955, 1-10.
Nozawa, S., Sakayori, M., Ohta, K., Iizuka, R., Mochizuki, H., Soma, M., Fujimoto, J., Hata., Iwamori, M. & Nagai, Y. (1989) A monoclonal antibody (MSN-1) against a newly established uterine endometrial cancer cell line (SNG-II) and its application to immunohistochemistry and flow cytometry. Am J Obster Gynecol 161, 1079-86.
Oku, N., Asai, T., Watanabe, K., Kuromi, K., Nagatsuka, M., Kurohane, K., Kikkawa, H., Ogino, K., Tantak, M., Ishikawa, D., Tsukada, H., Momose, M., Nakayama, J. & Taki, T. (2002) Anti-neovascular therapy using novel peptides homing to angiogenic vessels. Oncogene 1, 2662-9.
Pasqualini, R. & Ruoslahti, E. (1996) Organ targeting in vivo using phage display peptide libraries. Nature 380, 364-6.
Paswualini, R., Koivunen, E., Kain, R., Lahdenranta, J., Sakamoto, M., Stryhn, A., Ashmun, R. A., Shapiro, L. H., Arap, W. & Ruoslahti, E. (2000) Aminopeptidase N is a receptor for tumor-homing peptides and a target for inhibiting angiogenesis. Cancer Res 60, 722-7.
Rajotte, D. & Ruoslahti, E. (1999) Membrane dipeptidase is the receptor for a lung-targeting peptide identified by in vivo phage display. J.Biol.Chem. 274, 11593-11598.
Rajotte, D., Arap, W., Hagedorn, M., Kolvunen, E., Pasqualini, R. & Ruoslahti, E. (1998) Molecular heterogeneity of the vascular endothelium revealed by in vivo phage display. J. Clin Invest 102, 430-437.
Rasmussen, U. B., Schreiber, V., Schultz, H., Mischler, F. & Schughart, K. (2002) Tumor cell-targeting by phage-displayed peptides. Cancer Gene Ther 9, 606-12.
Ruoslahti, E. (2000) Targeting tumor vasculature with homing peptides from phage display. Semin Cancer Biol 10, 435-42.
Ruoslahti, E. (2002) Drug targeting to specific vascular sites. Drug Discov Today 7, 1138-43.
Smith, G. P. (1985) Filamentous fusion phage: novel expression vectors that display cloned antigens on the virion surface. Science 228, 1315-7.
Stausbol-Gron, B., Wind, T., Kjaer, S., Kahns, L., Hansen, N. J., Kristensen, P. & Clark, B. F. (1996) A model phage display subtraction method with potential for analysis of differential gene expression. FEBS Lett 391, 71-5.
Thomas, E. J. & Campbell, I. G. (2000) Evidence that Endometriosis Behaves in a Malignant Manner Gynecol Obstet Invest 50 Suppl 1, 2-10.
Torchilin, V. P., Rammohan, R., Weissig, V., and Levchenko, T. S. TAT peptide on the surface of liposomes affords their efficient intracellular delivery even at low temperature and in the presence of metabolic inhibitors. Proc Natl Acad Sci U S A, 98: 8786-8791, 2001.
Traish, A. M. & Wotiz, H. H. (1990) Monoclonal and polyclonal antibodies to human progesterone receptor peptide-(533-547) recognize a specific site in unactivated (8S) and activated (4S) progesterone receptor and distinguish between intact and proteolyzed receptors.Endocrinology 127, 1167-75.
Vigano, P., Gaffuri, B., Somigliana, E., Busacca, M., Di Blasio, A. M. & Vignali, M. (1998) Expression of intercellular adhesion molecule (ICAM)-1 mRNA and protein is enhanced in endometriosis versus endometrial stromal cells in culture. Mol Hum Reprod 4, 1150-6.

* cited by examiner

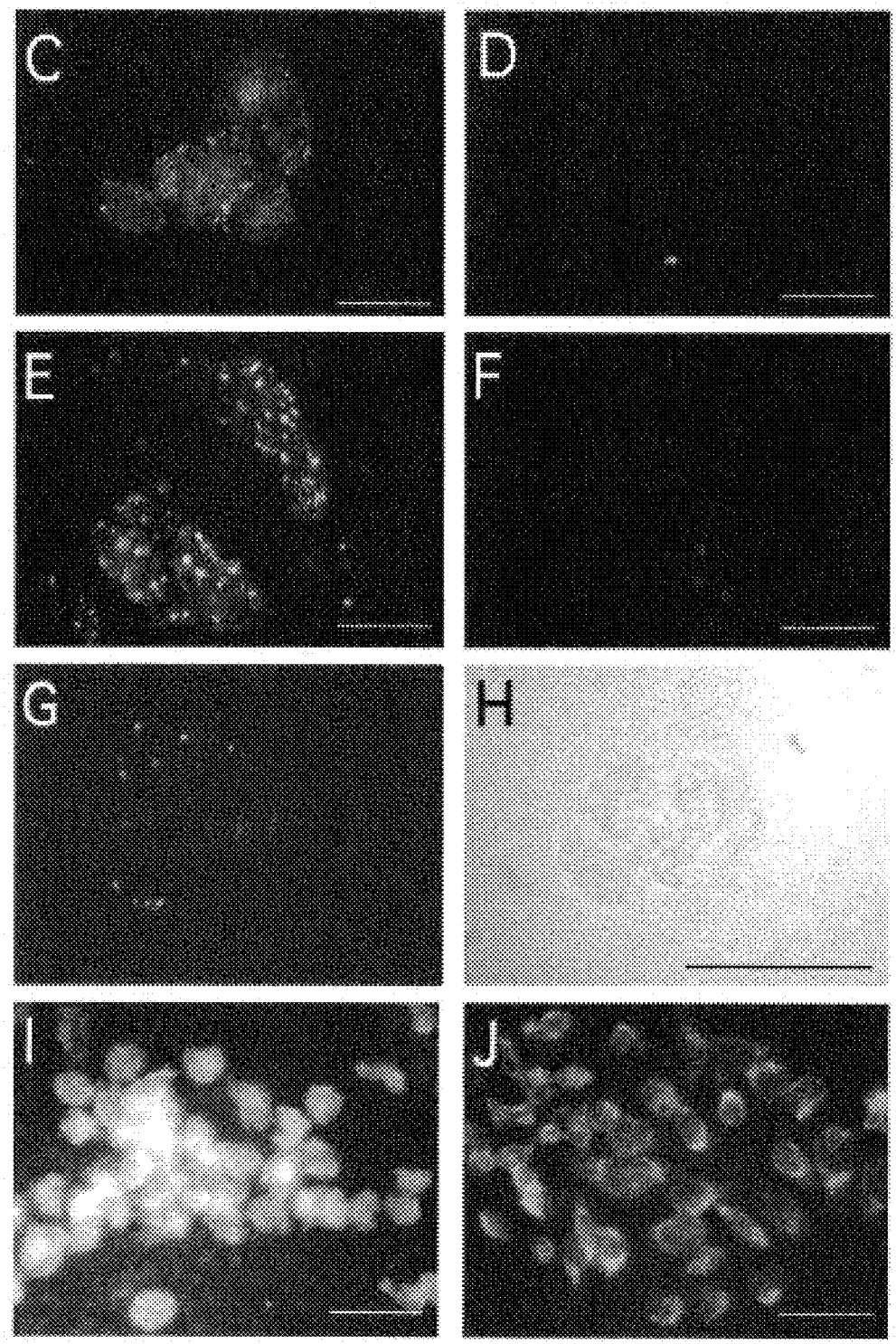
FIG. 2C-J

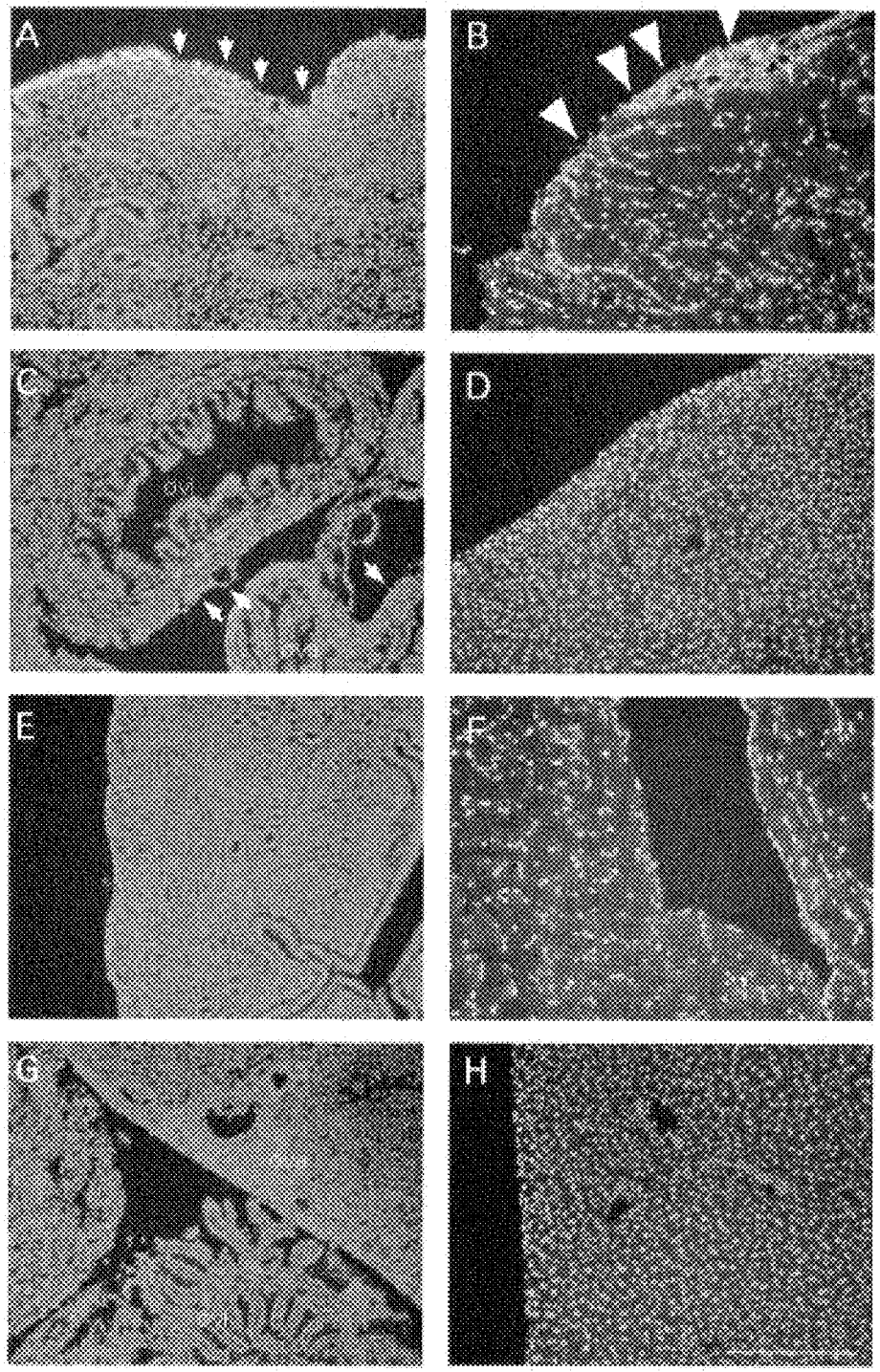
FIG. 3A-H

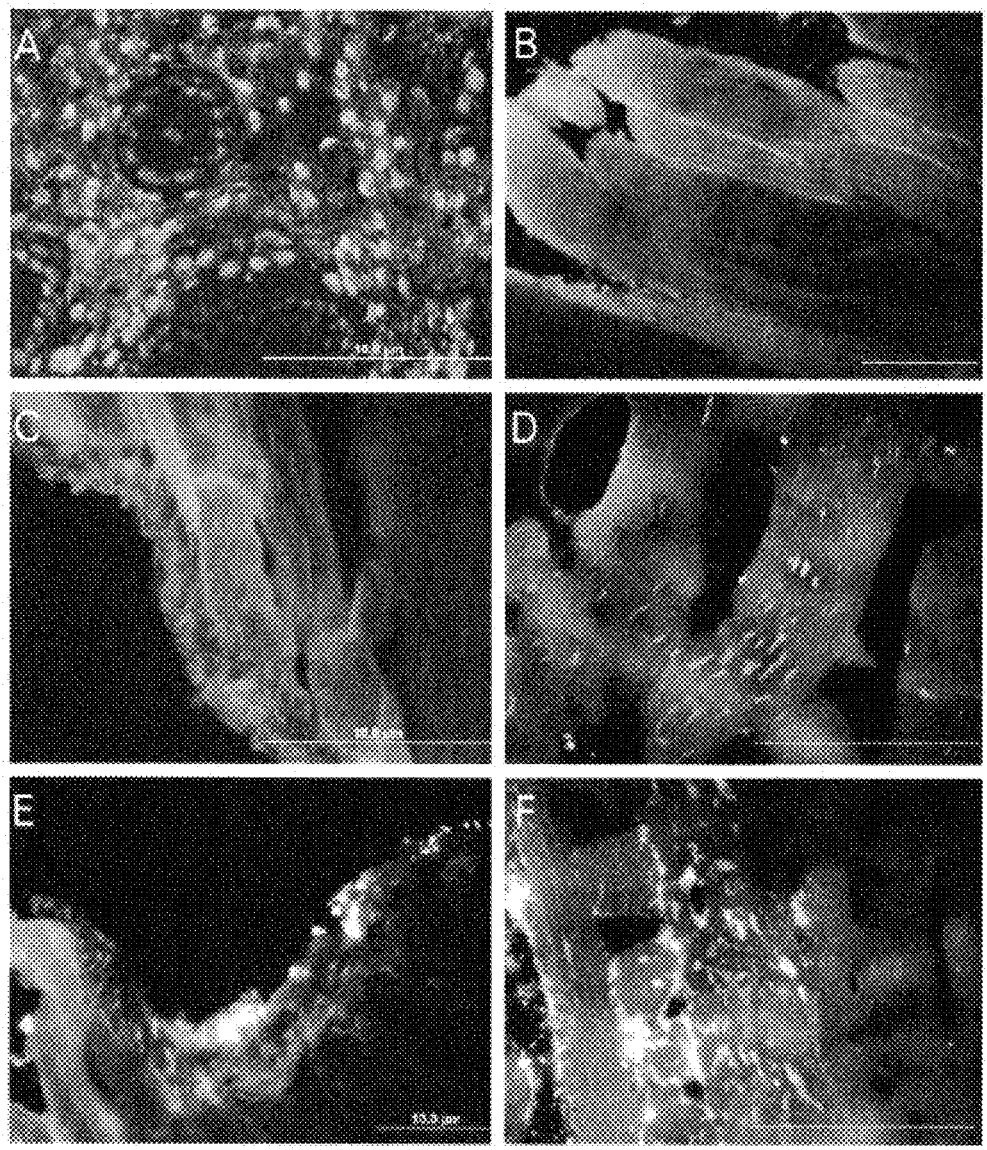
FIG. 4A-F

SEQUENCE LISTING

<160> NUMBER OF SEQ ID NOS: 25

<210> SEQ ID NO 1
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 1

Val Arg Arg Ala Xaa Asn Xaa Pro Gly
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic construct

<400> SEQUENCE: 2

Val Arg Arg Ala Asn Asn Leu Pro Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic construct

<400> SEQUENCE: 3

Val Arg Arg Ala Asp Asn Arg Pro Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic construct

<400> SEQUENCE: 4

Val Arg Arg Ala Asn Asn Arg Pro Gly
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic construct

<400> SEQUENCE: 5

Cys Arg Gly Met Ser Asp Thr Thr Ala Leu
1               5                   10

<210> SEQ ID NO 6
<211> LENGTH: 10
<212> TYPE: PRT

```
<213> ORGANISM: Artificial Sequence
<220> FEATURE:
<223> OTHER INFORMATION: Synthetic construct

<400> SEQUENCE: 6

Cys Val Arg Arg Ala Asp Asn Arg Pro Gly
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic construct

<400> SEQUENCE: 7

Val Arg Ser Ser Arg Ser Thr Pro Gln
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic construct

<400> SEQUENCE: 8

Met Gln Arg Thr Arg Ala Thr Pro Gly
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic construct

<400> SEQUENCE: 9

Arg Gly Met Ser Asp Thr Thr Ala Leu
1               5

<210> SEQ ID NO 10
<211> LENGTH: 16
<212> TYPE: PRT
<213> ORGANISM: Artificial Sequence
<220> FEATURE:
<223> OTHER INFORMATION: Synthetic construct

<400> SEQUENCE: 10

Arg Gln Pro Lys Ile Trp Phe Pro Asn Arg Arg Lys Pro Trp Lys Lys
1               5                   10                  15

<210> SEQ ID NO 11
<211> LENGTH: 11
<212> TYPE: PRT
<213> ORGANISM: Artificial Sequence
<220> FEATURE:
<223> OTHER INFORMATION: Synthetic construct

<400> SEQUENCE: 11

Gly Arg Lys Lys Arg Arg Gln Arg Pro Pro Gln
1               5                   10

<210> SEQ ID NO 12
<211> LENGTH: 16
<212> TYPE: PRT
<213> ORGANISM: Artificial Sequence
```

<220> FEATURE:
<223> OTHER INFORMATION: Synthetic construct

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic construct

<400> SEQUENCE: 13

Arg Gln Ile Ala Ile Trp Phe Gln Asn Arg Arg Met Lys Trp Ala Ala
1               5                   10                  15

<210> SEQ ID NO 14
<211> LENGTH: 9
<212> TYPE: PRT
<213> ORGANISM: Artificial Sequence
<220> FEATURE:
<223> OTHER INFORMATION: Synthetic construct

<400> SEQUENCE: 14

Arg Lys Lys Arg Arg Gln Arg Arg Arg
1               5

<210> SEQ ID NO 15
<211> LENGTH: 21
<212> TYPE: PRT
<213> ORGANISM: Artificial Sequence
<220> FEATURE:
<223> OTHER INFORMATION: Synthetic construct

<400> SEQUENCE: 15

Thr Arg Ser Ser Arg Ala Gly Leu Gln Phe Pro Val Gly Arg Val His
1               5                   10                  15

Arg Leu Leu Arg Lys
            20

<210> SEQ ID NO 16
<211> LENGTH: 26
<212> TYPE: PRT
<213> ORGANISM: Artificial Sequence
<220> FEATURE:
<223> OTHER INFORMATION: Synthetic construct

<400> SEQUENCE: 16

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 17
<211> LENGTH: 18
<212> TYPE: PRT
<213> ORGANISM: Artificial Sequence
<220> FEATURE:
<223> OTHER INFORMATION: Synthetic construct

<400> SEQUENCE: 17

Lys Leu Ala Leu Lys Leu Ala Leu Lys Ala Leu Lys Ala Ala Leu Lys
1               5                   10                  15

Leu Ala

<210> SEQ ID NO 18
<211> LENGTH: 16
<212> TYPE: PRT
<213> ORGANISM: Artificial Sequence
<220> FEATURE:
<223> OTHER INFORMATION: Synthetic construct

<400> SEQUENCE: 18

Ala Ala Val Ala Leu Leu Pro Ala Val Leu Leu Ala Leu Leu Ala Pro
1               5                   10                  15

<210> SEQ ID NO 19
<211> LENGTH: 10
<212> TYPE: PRT
<213> ORGANISM: Artificial Sequence
<220> FEATURE:
<223> OTHER INFORMATION: Synthetic construct

<400> SEQUENCE: 19

Val Pro Met Leu Lys Pro Met Leu Lys Glu
1               5                   10

<210> SEQ ID NO 20
<211> LENGTH: 28
<212> TYPE: PRT
<213> ORGANISM: Artificial Sequence
<220> FEATURE:
<223> OTHER INFORMATION: Synthetic construct

<400> SEQUENCE: 20

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 21
<211> LENGTH: 18
<212> TYPE: PRT
<213> ORGANISM: Artificial Sequence
<220> FEATURE:
<223> OTHER INFORMATION: Synthetic construct

<400> SEQUENCE: 21

Leu Leu Ile Ile Leu Arg Arg Arg Ile Arg Lys Gln Ala His Ala His
1               5                   10                  15

Ser Lys

<210> SEQ ID NO 22
<211> LENGTH: 21
<212> TYPE: PRT
<213> ORGANISM: Artificial Sequence
<220> FEATURE:
<223> OTHER INFORMATION: Synthetic construct

<400> SEQUENCE: 22

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 23
<211> LENGTH: 18
<212> TYPE: PRT

```
<213> ORGANISM: Artificial Sequence
<220> FEATURE:
<223> OTHER INFORMATION: Synthetic construct

<400> SEQUENCE: 23

Arg Gly Gly Arg Leu Ser Tyr Ser Arg Arg Phe Ser Thr Ser Thr
1               5                   10                  15

Gly Arg

<210> SEQ ID NO 24
<211> LENGTH: 15
<212> TYPE: PRT
<213> ORGANISM: Artificial Sequence
<220> FEATURE:
<223> OTHER INFORMATION: Synthetic construct

<400> SEQUENCE: 24

Ser Asp Leu Trp Glu Met Met Met Val Ser Leu Ala Cys Gln Tyr
1               5                   10                  15

<210> SEQ ID NO 25
<211> LENGTH: 12
<212> TYPE: PRT
<213> ORGANISM: Artificial Sequence
<220> FEATURE:
<223> OTHER INFORMATION: Synthetic construct

<400> SEQUENCE: 25

Thr Ser Pro Leu Asn Ile His Asn Gly Gln Lys Leu
1               5                   10
```

ENDOMETRIOSIS CELL TARGETING PEPTIDE AND USES THEREOF

CROSS-REFERENCE TO RELATED APPLICATIONS

This application is a divisional of U.S. application Ser. No. 11/616,098, filed Dec. 26, 2006, which claims benefit of U.S. Provisional Application No. 60/753,677, filed Dec. 23, 2005. Application Ser. No. 11/616,098, filed Dec. 26, 2006, and Application No. 60/753,677, filed Dec. 23, 2005, are hereby incorporated herein by reference in their entirety.

STATEMENT REGARDING FEDERALLY SPONSORED RESEARCH

This invention was made with government support under Grant 5P01 CA071932 from the National Institutes of Health and Grant DAMD17-02-1-0311 from the Department of Defense. The government has certain rights in the invention.

REFERENCE TO SEQUENCE LISTING

The Sequence Listing submitted Apr. 10, 2015 as a text file named "SBMRI_2_8403," created on Apr. 6, 2015, and having a size of 6,516 bytes is hereby incorporated by reference pursuant to 37 C.F.R. § 1.52(e)(5).

BACKGROUND

Endometriosis is a commonly encountered gynecological disease requiring medical and/or surgical therapy and is associated with considerable morbidity in women of reproductive age in developed countries (Murphy, A. A., 2002; Barbieri, R. L. & Missmer, S., 2002). Endometriosis occurs in the pelvis, most commonly in the ovaries and areas covered with peritoneum. The most frequent symptoms of genital tract endometriosis are dysmenorrhea, dyspareunia, chronic pelvic pain, and infertility. Several symptoms and pathologies are seen in endometriosis patients: women with extensive endometriosis may have little or no pain, while women with minimal endometriosis may have disabling pelvic pain. It is not clear if endometriosis is causally linked to infertility, but many abnormalities in peritoneal, tubal, and endometrial function are thought to inhibit fertility. Despite the fact that many women suffer from this condition, little is known about its cause or consequences.

Retrograde menstruation through the Fallopian tubes into the pelvic cavity during the menstrual cycle is a major contributor to the pathogenesis of endometriosis. Additional factors such as weak natural killer cell activity, autoimmunity, environmental risk factors, and genetic risk factors contribute to the development and progression of this disease (Cramer, D. W. & Missmer, S. A., 2002). However, it is not clear whether any of these factors is primarily responsible for endometriosis. Although endometriosis invades in a manner similar to cancer cells (Thomas, E. J. & Campbell, I. G., 2000), histologies of endometriosis show that endometriosis lesions are composed of fairly normal endometrial cells. Thus it appears that endometriosis represents an ectopic transplantation of normal endometrium. Nonetheless, biochemical analysis suggests a difference in protein expression patterns between endometriosis and normal endometrium (Arici, A., et al., 2003; Vigano, P., et al., 1998). Provided herein are compositions and methods for specifically targeting endometriosis cells.

BRIEF SUMMARY

Provided herein are compositions comprising a targeting peptide that selectively binds an endometriosis cell.

Also provided herein are methods comprising administering to a subject a composition comprising a targeting peptide that selectively binds an endometriosis cell.

Also provided herein are methods of targeting an endometriosis cell in a subject, the method comprising administering to the subject a composition comprising a targeting peptide that selectively binds an endometriosis cell.

Also provided herein are methods of detecting endometriosis in a subject, the method comprising administering to the subject a composition comprising a targeting peptide that selectively binds an endometriosis cell and detecting the composition in the subject, thereby detecting endometriosis.

Also provided herein are methods of diagnosing endometriosis in a subject, the method comprising administering to the subject a composition comprising a targeting peptide that selectively binds an endometriosis cell and detecting the composition in the subject, thereby diagnosing endometriosis in the subject.

Also provided herein are methods of determining the prognosis of endometriosis in a subject, the method comprising administering to the subject a composition comprising a targeting peptide that selectively binds an endometriosis cell and detecting the composition in the subject, wherein the level, amount, concentration, or a combination of binding of the composition to endometriosis tissue in the subject indicates the prognosis of the endometriosis in the subject.

Also provided herein are methods of determining the progress of endometriosis in a subject, the method comprising administering to the subject a composition comprising a targeting peptide that selectively binds an endometriosis cell, detecting the composition in the subject, and repeating the administration and detection at a later time, wherein a change in the level, amount, concentration, or a combination of binding of the composition to endometriosis tissue in the subject indicates the progress of the endometriosis in the subject.

Also provided herein are methods of determining the progress of treatment of endometriosis in a subject, the method comprising administering to the subject a composition comprising a targeting peptide that selectively binds an endometriosis cell, detecting the composition in the subject, and repeating the administration and detection following treatment, wherein a change in the level, amount, concentration, or a combination of binding of the composition to endometriosis tissue in the subject indicates the progress the treatment of the endometriosis in the subject.

Additional advantages of the disclosed methods and compositions will be set forth in part in the description which follows, and in part will be understood from the description, or may be learned by practice of the disclosed methods and compositions. The advantages of the disclosed methods and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed methods and compositions and together with the description, serve to explain the principles of the disclosed methods and compositions.

FIG. 1A shows steps of library screening including subtraction by the mouse peritoneum and adhesion/internalization on Ishikawa cell mono layers are shown. FIG. 1B shows binding efficiency to Ishikawa cells of phage pools obtained after each round of library screening. FIGS. 1C and 1D show phage overlay on frozen sections of human uterine endometriosis (FIG. 1C) and human liver (FIG. 1D). The phage pool obtained after three rounds of library screening was overlayed on frozen sections. Phage binding was visualized by immunohistochemistry with rabbit anti-T7 phage antibody by immunoperoxidase. Counter staining was done with hematoxylin. Arrowheads show positive staining of apical membranes of endometrial glandular epithelia. Asterisks show smooth muscle cells of the myometrium. Scale bar=100 µm.

FIGS. 2A-2J show in vitro binding of cloned phage and synthetic z13 peptide to cultured cells. FIG. 2A shows phage binding to Ishikawa cells and A431 control cells with phage z11, z12, z13, z15 and z24 clones. FIG. 2B shows Z13 phage binding to endometrial cells (1-5) and control cells (6-8). 1, Ishikawa; 2, SNG-II; 3, RL95-2; 4, Hec1A; 5, HES; 6, A431; 7, PC-3; 8, HeLa. In FIGS. 2A and 2B, phage was added to a monolayer of each cell line at 37° C. for 30 min. Internalized phage was counted by a plaque forming assay. FIGS. 2C and 2D show fluorescence micrographs of Ishikawa cells (FIG. 2C) and A431 cells (FIG. 2D) overlayed with z13 phage followed by immunostaining with anti-phage antibody and FITC conjugated anti-rabbit IgG antibody. FIGS. 2E and 2F show FITC-z13 peptide overlayed on Ishikawa cells (FIG. 2E) and A431 cells (FIG. 2F). FIGS. 2G and 2H show C16-z13 peptide-coated Qdot encapsulated liposomes overlayed on Ishikawa cells. Images of fluorescence (FIG. 2G) and phase contrast (FIG. 2H) are shown. FIGS. 2I and 2J are Qdot-cys-z13 (FIG. 2I) and Qdot-cys-m2 (FIG. 2J) overlayed on Ishikawa cells. Scale bar=10 µm.

FIGS. 3A-3H show targeting human endometriosis by z13 peptides in the SCID mouse. Qdot-z13 (FIG. 2E-2D) or control Qdot-m2 (FIG. 2F-2H) was injected into peritoneal cavity of the endometriosis mouse model, and distribution of Qdot after 30 min upon injection was determined by fluorescence microscopy. FIGS. 3A and 3E show human endometriosis transplant; FIGS. 3B and 3F show peritoneum; FIGS. 3C and 3G show oviduct and ovary; and FIGS. 3D and 3H show liver. Arrowheads show positive Qdot signals in mouse organs. ovi, oviduct; ova, ovary. Scale bar=20 µm.

FIGS. 4A to 4F show localization of human endometrial cells and Qdot-z13 targeting in the SCID mouse. FIG. 4A shows immunostaining of human endometriosis transplant using anti-PR antibody. FIG. 4B shows negative staining of control mouse peritoneum with anti-PR antibody. FIGS. 4C and 4D show positive immunostaining seen in the peritoneum of an endometriosis model mouse. FIGS. 4E and 4F show overlaps of Qdot-z13 and PR immunostaining in the peritoneum of the endometriosis model mouse. Scale bar=10 µm.

DETAILED DESCRIPTION

Figure 1A:
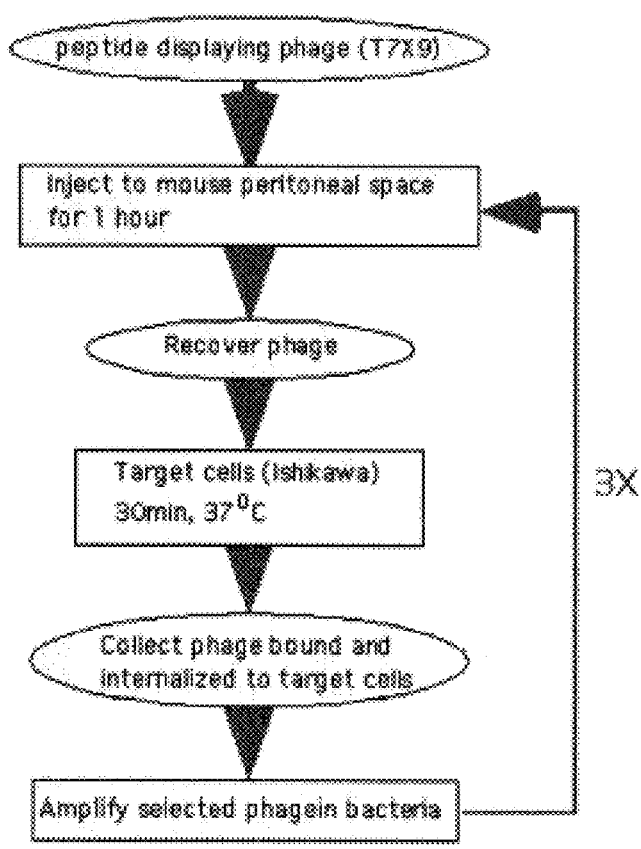
FIGS. 1A-1D show screening of peptide-displayed phage library.

The disclosed methods and compositions may be understood more readily by reference to the following detailed description of particular embodiments and the Example included herein and to the Figures and their previous and following description.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

A. Definitions

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps.

The terms "targeting" or "homing", as used herein can refer to the preferential movement, binding and/or accumulation of a targeted compound or composition, such as the disclosed compositions, at a site or a location as compared to a non-targeted compound or composition. For example, in the context of in vivo administration to a subject, "targeting" or "homing" can refer to the preferential movement, binding, and/or accumulation of a compound or composition, such as the disclosed compositions, in or at, for example, target tissue, target cells, and/or target structures as compared to non-target tissue, cells and/or structures.

The term "target tissue" as used herein refers to an intended site for accumulation of a targeted compound or composition, such as the disclosed compositions, following administration to a subject. For example, the methods of the presently disclosed subject matter employ a target tissue comprising endometriosis.

As used herein, "subject" includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. The subject may to an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. In the context of endometriosis and endometriosis cells, it is understood that a subject is a subject that has or can have endometriosis and/or endometriosis cells.

B. Targeting Peptides

Provided herein are compositions comprising a targeting peptide that selectively binds a cell. In some aspects, the cell is an endometriosis cell. As used herein, an "endometriosis cell" refers to an endometrial cell that is ectopically located. Endometriosis is believed to be largely the result of transplantation of viable cells exfoliated from the endometrium to ectopic locations. This reflux menstruation theory is based on the hypothesis that viable endometrial cells are introduced to the peritoneal cavity through retrograde menstruation through the oviducts.

When a cell is targeted, the cell can be targeted specifically or non-specifically. That is, the cell can be a target of the composition or substantially the only target. For example, when an endometriosis cell is targeted, the endometriosis cell can be targeted specifically (for example, with no substantial targeting of endometrial cells that are not endometriosis cells) or non-specifically (with targeting of endometrial and endometriosis cells). Thus, in some aspects, the cell is not an endometrial cell.

As used herein, a "targeting peptide" is peptide or polypeptide that binds to a target, such as a cell. For example, a targeting peptide can display selective targeting activity. The terms "selective targeting" or "selective homing" as used herein each refer to a preferential localization of a compound or composition, such as the disclosed compositions, that results in an amount of the compound or composition in a target tissue that is, for example, about 2-fold greater than an amount of the peptide in a control tissue, about 5-fold or greater, or about 10-fold or greater. For example, the terms "selective targeting" and "selective homing" can refer to binding or accumulation of a compound or composition, such as the disclosed compositions in a target tissue concomitant with an absence of targeting to a control tissue or the absence of targeting to all control tissues.

Generally, a targeting peptide, or segment thereof, must comprise at least 5, 6, 7, 8, 9 contiguous amino acids that confer specificity and affinity. The targeting peptide can comprise, for example, the amino acid sequence set forth in SEQ ID NOs:1, 2, 3 or 4. The targeting peptide can have at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the amino acid sequence set forth in SEQ ID NOs:1, 2, 3, or 4.

The targeting peptide can comprise, for example, an amino acid segment, wherein the segment has the amino acid sequence set forth in SEQ ID NOs:1, 2, 3, or 4. The targeting peptide can comprise an amino acid segment, wherein the segment has at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the amino acid sequence set forth in SEQ ID NOs:1, 2, 3, or 4. The amino acid segment can have at least 5, 6, 7, 8, or 9 consecutive amino acids. Thus, the amino acid segment can consist essentially of 5, 6, 7, 8, or 9 consecutive amino acids. Thus, the targeting peptide can consist essentially of at least 5, 6, 7, 8, or 9 consecutive amino acids.

The disclosed targeting peptides can be artificial sequences and can be synthesized in vitro and/or recombinantly. The disclosed targeting peptides can be peptides that are not naturally occurring protein and can be peptides that have at least two contiguous sequences that are not contiguous in a naturally occurring protein. The disclosed targeting peptides can be 5 to about 50 amino acids in length. The disclosed targeting peptides can be less than about 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, or 6 amino acids in length.

C. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

D. Protein Variants

The targeting peptide can comprise the amino acid sequence set forth in SEQ ID NOs:1, 2, 3, or 4, with one or more conservative amino acid substitutions. Thus, the targeting peptide can comprise the amino acid sequence set forth in SEQ ID NOs:1, 2, 3, or 4, with one, two or three conservative amino acid substitutions. As an example, the targeting peptide can comprise the amino acid sequence set forth in SEQ ID NOs:1, 2, 3, or 4, with one conservative amino acid substitution. The targeting peptide can also comprise an amino acid segment having the amino acid sequence set forth in SEQ ID NOs:1, 2, 3, or 4, with one or more conservative amino acid substitutions. Thus, the targeting peptide comprises an amino acid segment having the amino acid sequence set forth in SEQ ID NOs:1, 2, 3, or 4, with one, two or three conservative amino acid substitutions. As an example, the targeting peptide can comprises an amino acid segment having the amino acid sequence set forth in SEQ ID NOs:1, 2, 3, or 4, with one conservative amino acid substitution. The targeting peptide can comprise at least 6 contiguous amino acids from the amino acid sequence set forth in SEQ ID NOs:1, 2, 3, or 4. The targeting peptide can have at least 5, 6, 7, 8, or 9 consecutive amino acids. Thus, targeting peptide can consist of 5, 6, 7, 8, or 9 consecutive amino acids.

As discussed herein targeting peptides can include numerous variants based on a starting targeting peptide. Protein and peptide variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Table 2 and are referred to as conservative substitutions.

TABLE 2

Amino Acid Substitutions

| Original Residue | Exemplary Conservative Substitutions (others are known in the art) |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |

TABLE 2-continued

Amino Acid Substitutions

| Original Residue | Exemplary Conservative Substitutions (others are known in the art) |
|---|---|
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that the description of conservative mutations and homology can be combined together in any combination, such as embodiments that have at least 70% homology to a particular sequence wherein the variants are conservative mutations.

As this specification discusses various peptide sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent then the amino acids shown in Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH— (cis and trans), —$COCH_2$—, —CH(OH)$CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appin, EP 45665 CA (1982): 97:39405 (1982) (—CH(OH) $CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

E. Internalization Sequence

The provided compositions can further comprise a cellular internalization transporter or sequence. The Internalization sequence can be, for example, coupled to the targeting peptide or can be included in compositions containing the targeting peptide. The cellular internalization sequence can be any internalization sequence known or newly discovered in the art, or conservative variants thereof. Non-limiting examples of cellular internalization transporters and sequences include Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol) (see Table 1).

TABLE 1

Cell Internalization Transporters

| Name | Sequence | SEQ ID NO |
| --- | --- | --- |
| Antp | RQPKIWFPNRRKPWKK | (SEQ ID NO: 10) |
| HIV-Tat | GRKKRRQRPPQ | (SEQ ID NO: 11) |
| Penetratin | RQIKIWFQNRRMKWKK | (SEQ ID NO: 12) |
| Antp-3A | RQIAIWFQNRRMKWAA | (SEQ ID NO: 13) |
| Tat | RKKRRQRRR | (SEQ ID NO: 14) |
| Buforin II | TRSSRAGLQFPVGRVHRLLRK | (SEQ ID NO: 15) |
| Transportan | GWTLNSAGYLLGKINKALAALAKKIL | (SEQ ID NO: 16) |
| model amphipathic peptide (MAP) | KLALKLALKALKAALKLA | (SEQ ID NO: 17) |
| K-FGF | AAVALLPAVLLALLAP | (SEQ ID NO: 18) |
| Ku70 | VPMLK- PMLKE | (SEQ ID NO: 19) |
| Prion | MANLGYWLLALFVTMWTDVGLCKKRPKP | (SEQ ID NO: 20) |
| pVEC | LLIILRRRIRKQAHAHSK | (SEQ ID NO: 21) |
| Pep-1 | KETWWETWWTEWSQPKKKRKV | (SEQ ID NO: 22) |
| SynB1 | RGGRLSYSRRRFSTSTGR | (SEQ ID NO: 23) |

TABLE 1-continued

Cell Internalization Transporters

| Name | Sequence | SEQ ID NO |
|---|---|---|
| Pep-7 | SDLWEMMMVSLACQY | (SEQ ID NO: 24) |
| HN-1 | TSPLNIHNGQKL | (SEQ ID NO: 25) |
| BGSC (Bis-Guanidinium-Spermidine-Cholesterol) | [chemical structure of BGSC] | |
| BGTC (Bis-Guanidinium-Tren-Cholesterol) | [chemical structure of BGTC] | |

Thus, the provided targeting peptide can further comprise the amino acid sequence SEQ ID NO:10, SEQ ID NO:11 (Bucci, M. et al. 2000. Nat. Med. 6, 1362-1367), SEQ ID NO:12 (Derossi, D., et al. 1994. Biol. Chem. 269, 10444-10450), SEQ ID NO:13 (Fischer, P. M. et al. 2000. J. Pept. Res. 55, 163-172), SEQ ID NO:14 (Frankel, A. D. & Pabo, C. O. 1988. Cell 55, 1189-1193; Green, M. & Loewenstein, P. M. 1988. Cell 55, 1179-1188), SEQ ID NO:15 (Park, C. B., et al. 2000. Proc. Natl Acad. Sci. USA 97, 8245-8250), SEQ ID NO:16 (Pooga, M., et al. 1998. FASEB J. 12, 67-77), SEQ ID NO:17 (Oehlke, J. et al. 1998. Biochim. Biophys. Acta. 1414, 127-139), SEQ ID NO:18 (Lin, Y. Z., et al. 1995. J. Biol. Chem. 270, 14255-14258), SEQ ID NO:19 (Sawada, M., et al. 2003. Nature Cell Biol. 5, 352-357), SEQ ID NO:20 (Lundberg, P. et al. 2002. Biochem. Biophys. Res. Commun 299, 85-90), SEQ ID NO:21 (Elmquist, A., et al. 2001. Exp. Cell Res. 269, 237-244), SEQ ID NO:22 (Morris, M. C., et al. 2001. Nature Biotechnol. 19, 1173-1176), SEQ ID NO:23 (Rousselle, C. et al. 2000. Mol. Pharmacol. 57, 679-686), SEQ ID NO:24 (Gao, C. et al. 2002. Bioorg. Med. Chem. 10, 4057-4065), or SEQ ID NO:25 (Hong, F. D. & Clayman, G. L. 2000. Cancer Res. 60, 6551-6556). The provided polypeptide can further comprise BGSC (Bis-Guanidinium-Spermidine-Cholesterol) or BGTC (Bis-Guanidinium-Tren-Cholesterol) (Vigneron, J. P. et al. 1998. Proc. Natl. Acad. Sci. USA. 93, 9682-9686). The preceding references are hereby incorporated herein by reference in their entirety and for their teachings of cellular internalization vectors and sequences. Any other internalization sequences now known or later identified can be combined with a polypeptide disclosed herein.

F. Effectors

The herein provided compositions can further comprise an effector molecule. By "effector molecule" is meant a substance that acts upon the target cell(s) or tissue to bring about a desired effect. The effect can, for example, be the labeling, activating, repressing, or killing of the target cell(s) or tissue. Thus, the effector molecule can, for example, be a small molecule, pharmaceutical drug, toxin, fatty acid, detectable marker, conjugating tag, nanoparticle, or enzyme.

Examples of small molecules and pharmaceutical drugs that can be conjugated to a targeting peptide are known in the art. The effector can be a cytotoxic small molecule or drug that kills the target cell. The small molecule or drug can be designed to act on any critical cellular function or pathway. For example, the small molecule or drug can inhibit the cell cycle, activate protein degradation, induce apoptosis, modulate kinase activity, or modify cytoskeletal proteins. Any known or newly discovered cytotoxic small molecule or drugs is contemplated for use with the targeting peptides.

The effector can be a toxin that kills the targeted cell. Non-limiting examples of toxins include abrin, modeccin, ricin and diphtheria toxin. Other known or newly discovered toxins are contemplated for use with the targeting peptides.

Fatty acids (i.e., lipids) that can be conjugated to the targeting peptide include those that allow the efficient incorporation of the peptide into liposomes. Generally, the fatty acid is a polar lipid. Thus, the fatty acid can be a phospholipid The provided compositions can comprise either natural or synthetic phospholipid. The phospholipids can be selected from phospholipids containing saturated or unsaturated mono or disubstituted fatty acids and combinations thereof. These phospholipids can be dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Alabaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided compositions can comprise palmitoyl 16:0.

Detectable markers include any substance that can be used to label or stain a target tissue or cell(s). Non-limiting examples of detectable markers include radioactive isotopes, enzymes, fluorochromes, and quantum dots (Qdot®). Other known or newly discovered detectable markers are contemplated for use with the targeting peptides.

The effector molecule can be a nanoparticle, such as a heat generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Nanoshells can be formed with a core of a dielectric or inert material such as silicon, coated with a material such as a highly conductive metal which can be excited using radiation such as near infrared light (approximately 800 to 1300 nm). Upon excitation, the nanoshells emit heat. The resulting hyperthermia can kill the surrounding cell(s) or tissue. The combined diameter of the shell and core of the nanoshells ranges from the tens to the hundreds of nanometers. Near infrared light is advantageous for its ability to penetrate tissue. Other types of radiation can also be used, depending on the selection of the nanoparticle coating and targeted cells. Examples include x-rays, magnetic fields, electric fields, and ultrasound. The problems with the existing methods for hyperthermia, especially for use in cancer therapy, such as the use of heated probes, microwaves, ultrasound, lasers, perfusion, radiofrequency energy, and radiant heating is avoided since the levels of radiation used as described herein is insufficient to induce hyperthermia except at the surface of the nanoparticles, where the energy is more effectively concentrated by the metal surface on the dielectric. The particles can also be used to enhance imaging, especially using infrared diffuse photon imaging methods. Targeting molecules can be antibodies or fragments thereof, ligands for specific receptors, or other proteins specifically binding to the surface of the cells to be targeted.

The effector molecule can be covalently linked to the targeting peptide. The effector molecule can be linked to the amino terminal end of the targeting peptide. The effector molecule can be linked to the carboxy terminal end of the targeting peptide. The effector molecule can be linked to an amino acid within the targeting peptide. The herein provided compositions can further comprise a linker connecting the effector molecule and targeting peptide. The targeting peptide can also be conjugated to a coating molecule such as bovine serum albumin (BSA) (see Tkachenko et al., (2003) J Am Chem Soc, 125, 4700-4701) that can be used to coat the Nanoshells with the peptide.

Protein crosslinkers that can be used to crosslink the effector molecule to the targeting peptide are known in the art and are defined based on utility and structure and include DSS (Disuccinimidylsuberate), DSP (Dithiobis(succinimidylpropionate)), DTSSP (3,3'-Dithiobis(sulfosuccinimidylpropionate)), SULFO BSOCOES (Bis[2-(sulfosuccinimdooxycarbonyloxy)ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl)aminobenzoate), SULFO SIAB (N-Sulfosuccinimidyl(4-iodoacetyl)aminobenzoate), SMCC (Succinimidyl-4-(N-maleimidomethyl)cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS (N-(epsilon-Maleimidocaproyloxy) sulfosuccinimide), EMCS (N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), DMA (Dimethyladipimidate hydrochloride).

The herein provided compositions can further comprise a progestational agent. Thus, the compositions can comprise Danazol, medroxyprogesterone acetate, norethynodrel, megestrol acetate, dydrogesterone, norethisterone, or lynestrenol. The provided compositions can further comprise a Gonadotropin-releasing hormone (GnRH), GnRH analog, or GnRH agonist. Thus, the compositions can comprise leuprorelin, nafarelin, goserelin, buserelin, or triptorelin. The compositions can further comprise an aromatase inhibitor. Thus, the compositions can comprise letrozole or anasrozole. The compositions can further comprise a narcotic. The compositions can further comprise a non-steroidal anti-inflammatory drug (NSAID). Thus the compositions can comprise ibuprofen, naproxen, nurofen, ponstan, or voltaren.

1. Pharmaceutical Carriers

The herein disclosed targeting peptides can be administered in vivo in a pharmaceutically acceptable carrier. Thus, the provided compositions can further comprise a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The provided compositions can be in solution, suspension (for example, incorporated into microparticles, liposomes, or cells). The provided compositions can further be combined with antibodies, receptors, or receptor ligands to direct internalization of the composition into the targeted endometriosis cell. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

2. Nucleic Acids

Provided herein are isolated nucleic acids comprising a nucleic acid sequence encoding a targeting peptide that selectively binds an endometriosis cell. The nucleic acid sequence can encode the amino acid sequence set forth in SEQ ID NOs:1, 2, 3, or 4. The nucleic acid can further comprises a nucleic acid sequence encoding an effector molecule. For example, the effector molecule can be any polypeptide effector disclosed herein. The nucleic acid sequence encoding the effector molecule can be 5' to the nucleic acid sequence encoding the targeting peptide. The nucleic acid sequence encoding the effector molecule can be 3' to the nucleic acid sequence encoding the targeting peptide. The nucleic acid can encode a fusion protein comprising the targeting peptide and the effector molecule.

3. Antibodies

Also provided herein are antibodies specific for the herein provided targeting peptides. The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with the targeting peptide such that the targeting peptide is inhibited from interacting with the target cell. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

G. Methods

1. Cell Targeting and Detection

Also provided herein are methods comprising administering to a subject a composition comprising a targeting peptide that selectively binds a cell. In one aspect, the cell is an endometriosis cell. In another aspect, the cell is not an endometrial cell. The subject can comprise the cell. Thus, the subject can comprise an endometriosis cell.

The targeting peptide of the provided methods can be any of the herein disclosed targeting peptides. Thus, the targeting peptide can comprise the amino acid sequence set forth in SEQ ID NOs:1, 2, 3, or 4. The targeting peptide can have at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the amino acid sequence set forth in SEQ ID NOs:1, 2, 3, or 4. The targeting peptide can comprise the amino acid sequence set forth in SEQ ID NOs:1, 2, 3, or 4 with one or more conservative amino acid substitutions. The composition of the provided methods can further comprise an effector molecule. Thus, the effector molecule is a small molecule, pharmaceutical drug, toxin, fatty acid, detectable marker, nanoparticle or enzyme.

Also provided herein are methods of targeting an endometriosis cell in a subject, the method comprising administering to the subject a composition comprising a targeting peptide that selectively binds an endometriosis cell. The cell can be an endometriosis cell. The targeting peptide can comprises the amino acid sequence set forth in SEQ ID NOs:1, 2, 3, or 4. The targeting peptide can have at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the amino acid sequence set forth in SEQ ID NOs:1, 2, 3, or 4. The targeting peptide can comprise the amino acid sequence set forth in SEQ ID NOs:1, 2, 3, or 4 with one or more conservative amino acid substitutions.

The composition of the provided methods can further comprise an effector molecule. Thus, the effector molecule can be a small molecule, pharmaceutical drug, toxin, fatty acid, detectable marker, nanoparticle or enzyme. The composition of the methods can comprise a progestational agent. Thus, the composition can comprise Danazol, medroxyprogesterone acetate, norethynodrel, megestrol acetate, dydrogesterone, norethisterone, or lynestrenol. The composition can further comprise a Gonadotropin-releasing hormone (GnRH), GnRH analog, or GnRH agonist. Thus, the composition can comprise leuprorelin, nafarelin, goserelin, buserelin, or triptorelin. The composition can further comprise an aromatase inhibitor. Thus, the composition can comprise letrozole or anasrozole. The composition can further comprise a narcotic. The composition can further comprise a non-steroidal anti-inflammatory drug (NSAID). Thus the composition can comprise ibuprofen, naproxen, nurofen, ponstan, or voltaren.

Also provided herein are methods of detecting endometriosis in a subject, the method comprising administering to the subject a composition comprising a targeting peptide that selectively binds an endometriosis cell and detecting the composition in the subject, thereby detecting endometriosis. For example, the composition can comprise a label or other detectable moiety or molecule (as the effector, for example) and the composition can be detected by, for example, detecting the label or other detectable moiety or molecule. The presence, location, pattern or other characteristics of the detected composition can be used as an indicator that the subject has endometriosis.

Also provided herein are methods of diagnosing endometriosis in a subject, the method comprising administering to the subject a composition comprising a targeting peptide that selectively binds an endometriosis cell and detecting the composition in the subject, thereby diagnosing endometriosis in the subject. For example, the composition can comprise a label or other detectable moiety or molecule (as the effector, for example) and the composition can be detected by, for example, detecting the label or other detectable moiety or molecule. The presence, location, pattern or other characteristics of the detected composition can be used as an indicator that the subject has endometriosis.

Also provided herein are methods of determining the prognosis of endometriosis in a subject, the method comprising administering to the subject a composition comprising a targeting peptide that selectively binds an endometriosis cell and detecting the composition in the subject, wherein the level, amount, concentration, or a combination of binding of the composition to endometriosis tissue in the subject indicates the prognosis of the endometriosis in the subject. For example, the composition can comprise a label or other detectable moiety or molecule (as the effector, for example) and the composition can be detect by, for example, detecting the label or other detectable moiety or molecule. The presence, location, pattern or other characteristics of the detected composition can be used as an indicator of the severity and/or future progress of the endometriosis.

Also provided herein are methods of determining the progress of endometriosis in a subject, the method comprising administering to the subject a composition comprising a targeting peptide that selectively binds an endometriosis cell, detecting the composition in the subject, and repeating the administration and detection at a later time, wherein a change in the level, amount, concentration, or a combination of binding of the composition to endometriosis tissue in the subject indicates the progress of the endometriosis in the subject. For example, the composition can comprise a label or other detectable moiety or molecule (as the effector, for example) and the composition can be detected by, for example, detecting the label or other detectable moiety or molecule. A change in the presence, location, pattern or other characteristics of the detected composition can be used as an indicator of the progress of the endometriosis.

Also provided herein are methods of determining the progress treatment of endometriosis in a subject, the method comprising administering to the subject a composition comprising a targeting peptide that selectively binds an endometriosis cell, detecting the composition in the subject, and repeating the administration and detection following treatment, wherein a change in the level, amount, concentration, or a combination of binding of the composition to endometriosis tissue in the subject indicates the progress the treatment of the endometriosis in the subject. For example, the composition can comprise a label or other detectable moiety or molecule (as the effector, for example) and the composition can be detected by, for example, detecting the label or other detectable moiety or molecule. A change in the presence, location, pattern or other characteristics of the detected composition can be used as an indicator of the progress treatment of the endometriosis.

The targeting peptide of the herein provided methods of detection and diagnosis can be linked to a detectable marker, such as those known in the art or disclosed herein. The detectable markers can be detected using standard methods known in the art.

The disclosed compositions can also be used in a variety of ways as research tools. For example, the disclosed compositions, such as SEQ ID NOs:1, 2, 3, or 4, can be used to study protein expression by endometriosis cells. This can be accomplished by, for example, isolating or sorting cells based on the binding of the disclosed compositions to the cell. The disclosed compositions can also be used diagnostic tools related to endometriosis. The disclosed compositions can also be used as either reagents in micro arrays or as reagents to probe or analyze existing microarrays.

2. Administration

The compositions may be administered orally, parenterally (e.g., intravenously), by intramuscular injection, by intraperitoneally, transdermally, extracorporeally, topically or the like, including topical intranasal administration or administration by inhalant. For example, the provided compositions can be administered into a subject's peritoneal cavity during laparoscopy. Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, extent of the disease in the patient, hormonal conditions, route of administration, or whether other drugs are included in the regimen, and can be determined by one of skill in the art. The dosage can be adjusted by the individual physician in the event of any counterindications. Dosage can vary for one or several days. Guidance can be found in the literature for appropriate dosages for given classes of pharmaceutical products. A typical daily dosage of the targeting peptides used as a therapeutic, such as nanoshell conjugate, can range from about 1 µg/kg to up to 1 mg/kg of body weight or more per day, depending on the factors mentioned above.

Following administration of a disclosed composition for treating, inhibiting, or preventing endometriosis, the efficacy of the therapeutic composition can be assessed in various ways well known to the skilled practitioner. For instance, one of ordinary skill in the art will understand that a composition disclosed herein is efficacious in treating or inhibiting endometriosis in a subject by evaluating CA19-9 and CA125 antigens in the patient's sera. Serum CA19-9 and CA125 antigens can serve as diagnosis marker for endometriosis (Harada T. et al., 2002. Usefulness of CA19-9 versus CA125 for the diagnosis of endometriosis. Fertil. Steril. 78: 733-739). Antigen levels can also be used to monitor a patient's progress. An alternative method for evaluating treatment involves pathological examination of biopsy samples collected by laparoscopy.

The compositions disclosed herein and the compositions necessary to perform the disclosed methods can be made using any method known to those of skill in the art for that particular reagent or compound unless otherwise specifically noted.

One method of producing the disclosed peptides, such as SEQ ID NOs:1, 2, 3, or 4, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

H. Methods of Making the Compositions

The compositions disclosed herein and the compositions necessary to perform the disclosed methods can be made using any method known to those of skill in the art for that particular reagent or compound unless otherwise specifically noted.

Disclosed are processes for making the compositions as well as making the intermediates leading to the compositions. For example, disclosed are nucleic acid molecules produced by the process comprising linking in an operative way a nucleic acid molecule comprising a sequence encoding a peptide set forth in SEQ ID NO:1, 2, 3, or 4 and a sequence controlling an expression of the nucleic acid molecule.

Disclosed are nucleic acid molecules produced by the process comprising linking in an operative way a nucleic acid molecule comprising a sequence encoding a peptide having 80% identity to a peptide set forth in SEQ ID NO:1, 2, 3, or 4 and a sequence controlling an expression of the nucleic acid molecule.

Disclosed are nucleic acids produced by the process comprising linking in an operative way a nucleic acid molecule comprising a sequence encoding a peptide having 80% identity to a peptide set forth in SEQ ID NO:1, 2, 3, or 4 wherein any change is a conservative change, and a sequence controlling an expression of the nucleic acid molecule.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally occurring disclosed nucleic acids.

Disclosed are animals produced by the process of transfecting a cell within the animal with any of the nucleic acid molecules disclosed herein. Disclosed are animals produced by the process of transfecting a cell within the animal with any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclosed are animals produced by the process of adding to the animal any of the cells disclosed herein.

1. Nucleic Acid Synthesis

The disclosed nucleic acids, such as the oligonucleotides to be used as primers, can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

2. Peptide Synthesis

One method of producing the disclosed proteins, such as SEQ ID NO:1, 2, 3, or 4, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

I. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example, disclosed are kits for diagnosing endometriosis. The kit can comprise a composition comprising a targeting peptide conjugated to a detectable marker and a means for detection. Detectable markers are known in the art and include, for example, enzymes, fluorescent molecules and proteins, and radioactive isotopes. Means for detection are also known in the art and depend on the selected marker.

J. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated. For example, disclosed and contemplated are systems comprising a composition comprising a targeting peptide conjugated to a nanoshell and a means for excitation of the nanoshell. Such means are known in the art.

EXAMPLES

1. Example 1

Materials and Methods

Phage Library and Antibodies.

A T7 phage library displaying random 9-mer peptide sequences constructed in the T7 Select 415-1b vector (Novagen) (Essler, M. & Ruoslahti, E., 2002). Polyclonal rabbit anti-T7 phage antibodies do not cross-react with frozen and paraffin sections of normal human and mouse tissues (Essler, M. & Ruoslahti, E., 2002).

Synthetic Peptides.

The following peptides were synthesized by AnaSpec, San Jose, Calif.: z13, VRRADNRPG (SEQ ID NO:3); cys-z13, CVRRADNRPG (SEQ ID NO:6); cys-m2, CRGMSDTTAL (SEQ ID NO:5); fluorescent FITC-z13, and fatty acid conjugated C16-z13. Each cys-z13 and cys-m2 was bound to fluorescent nanocrystal Qdot605 using a Qdot antibody conjugation kit (Quantum Dot, Hayward, Calif.), according to the manufacturer's protocol.

Preparation of Liposomes.

Twenty µl of C16-z13 peptide (10 mM in chloroform: methanol 2:1) was mixed with 20 µl phosphatidylcholine (100 mM in chloroform) and 10 µl cholesterol (100 mM in chloroform) in a round bottom flask and evaporated in a rotary evaporator. The sample was dried in a vacuum, dissolved in 500 µl 0.3M citric acid, and frozen and thawed three times, followed by sonication for 10 min. Five hundred µl of 0.2M $Na_2CO_3$ and 20 µl of 1 µM Qdot605 streptavidin was added and heated at 60° C. for 1 hour. After adding 1 ml of 20 mM Hepes buffer, pH7.2, the liposome solution was centrifuged at 90,000 rpm for 30 min at 4° C. and the pellet dissolved in PBS.

Cell Lines and Cell Culture.

A human endometrial adenocarcinoma cell line, Ishikawa (Lessey, B. A., et al., 1996; Castelbaum, A. J., et al., 1997) was obtained. The human endometrial epithelial cell line HES (Desai, N. N., et al., 1994) was obtained. The endometrial adenocarcinoma, SNG-II, was described previously (Nozawa, S., et al., 1989). Endometrial adenocarcinoma lines RL95-2 and Hec1A; the human squamous cell carcinoma A431; and human cervical carcinoma HeLa cells were obtained from American Tissue Culture Collection, Manassas, Va. All cells were cultured in Dulbecco's modified Eagle's medium with high glucose supplemented with 10% fetal calf serum, 2 mM glutamine, 1 mM pyruvate, 100 Units/ml penicillin, and 100 µg/ml streptomycin, at 37° C. in a humidified incubator under 5% $CO_2$.

Phage Library Screening.

A 6-week-old C57/BL6 female mouse was anesthetized with avertin, and 1 ml of a T7 phage library containing a total of $10^{11}$ clones was injected into the peritoneal cavity. After 30 min, the library was recovered by washing the peritoneal cavity with 10 ml PBS. This subtracted library was added to a monolayer of Ishikawa cells grown in a 3.5 cm tissue culture plate and incubated at 37° C. for 30 min, allowing bound phage to be internalized by endocytosis. Cells were washed 6 times with DME and detached by trypsinization. Cells were solubilized by 1% NP-40 in PBS, and competent BL21 bacteria were infected with the released phage. T7 phage was amplified in BL21 cells until lysis occurred. Amplified phage, $1\times10^7$ clones (1 ml), was subtracted again by the mouse peritoneum and selected by incubation with Ishikawa cells as described. This cycle was repeated three times. Binding of each cloned phage to target cells was determined by counting the number of phage plaques recovered from Ishikawa cells as a positive control or from A431 cells as a negative control. Sequencing of the phage clone was performed as described (Hoffman, J. A., et al., 2002).

Fluorescence Microscopy.

Ishikawa cells and A431 cells were grown on glass coverslips in 3.5 cm tissue culture plates. Each phage clone including z13 was added to these cells, incubated at 4° C. for 15 min, washed with cold PBS, and fixed with 1% paraformaldehyde (PFA) in PBS. Phage was detected using rabbit anti-T7 antibody and FITC-conjugated goat anti-rabbit IgG antibody. After washing three times with PBS, cells were fixed with 1% paraformaldehyde in PBS and inspected under a Zeiss Axioplan fluorescence microscope. Ishikawa cells grown on glass coverslips were incubated in medium containing FITC-z13 peptide (1 µg/ml) at 37° C. for 15 min. After washing with PBS, cells were fixed with 1% PFA in PBS, and inspected under the fluorescence microscope. Qdot-encapsulated and C16-z13 peptide coated liposomes were prepared as described above. Ishikawa cells were incubated with these liposomes at 37° C. for 15 min, washed with PBS, fixed with 1% PFA, and inspected under the fluorescence microscope. Qdot605-conjugated peptide, Qdot-cys-z13, or control peptide, Qdot-cys-m2, was added to the culture at 100 nM and left at 37° C. for 15 min.

For in vivo targeting, Qdot-cys-z13 or Qdot-cys-m2 (200 nmoles in 200 µl PBS/mouse) was injected into the peritoneum of a SCID mouse that had received intraperitoneal grafts of human endometrial tissues. The abdomen of the mouse was massaged gently to distribute injected material to the entire peritoneal cavity. After 30 min, mice were sacrificed, and the endometrial graft and organs facing the peritoneum were isolated. Tissues were washed in PBS, embedded in O. C. T. compound (Sakura Finetechnical, Tokyo, Japan) and cryosections were made. Sections were fixed with cold methanol, covered with Vecta-shield with DAPI (Vector), and inspected with a fluorescence microscope.

Immunohistochemistry for the progesterone receptor (PR) was performed as follows: Frozen mouse tissue sections prepared from Qdot-cys-z13 injected mice, Qdot-cys-m2 injected mice, and control mice without Qdot injection were fixed in cold methanol for 15 min. Tissue sections were blocked with avidin (5 ng/ml) in PBS at room temperature for 15 min, followed by incubation with 10% goat serum containing biotin (5 µg/ml) for 1 hour. The tissue sections were then applied to immunohistochemistry with a diluted (1:100) anti-PR antibody (DAKO, Carpinteria, Calif.) at 4° C. for 20 hours. After washing with PBS, sections were incubated with biotinylated anti-rabbit IgG antibody (Zymed) and by streptavidin conjugated Qdot565.

Phage Immunohistochemistry on Frozen Human Tissue Sections.

Human tissues including uterine endometriosis (adenomyosis) were obtained from patients, after obtaining written informed consent from each patient. The Institutional Review Board of Shinshu University School of Medicine approved the use of human subjects for this study. These tissue specimens were fixed with 20% buffered formalin (pH 7.4) for 48 hours and then incubated with a 0.88 M hypertonic gum sucrose solution overnight. They were immediately frozen in an O.C.T. compound at −80° C. and sliced at 6 µm thickness. The frozen sections were placed on slides and stored frozen until use. Phage was overlayed on the sections at room temperature for 30 min, washed with PBS and fixed with 1% paraformaldehyde in PBS. Immunohistochemistry of tissue sections was undertaken using rabbit anti-T7 phage antibody followed by immunoperoxidase reactions. Staining was visualized by DAB and hematoxylin was used for counterstaining.

Mouse model for peritoneal endometriosis. An endometriosis mouse model was constructed using the SCID mouse and human endometriosis tissues as described (Aoki, D., et al., 1994), except endometrial tissues were transplanted to the peritoneal wall. Briefly, human normal endometrial specimens were obtained during hysterectomy from patients who had undergone surgery for uterine myomas and ovarian cysts. Written informed consent was obtained from each patient. The use of human subjects for this study was approved by the Institutional Review Board of Keio University School of Medicine. After removing the myometrium from each specimen by gentle scraping, the remaining endometrium was cut into 2 mm cubes with a safety razor blade. Specimens were maintained in sterilized medium containing 30 ng/ml penicillin G (pH 7.4) until use. Each mouse under intraperitoneal anesthesia with avertin (50 mg/kg) was placed on its back and an incision about 2 cm in length was made in the abdomen. Two pieces of endometrial tissue, each a 2-mm cube, were grafted onto the peritoneal wall with absorbable suture material. Animals were maintained for up to 10 weeks.

Results

Identification of Phage Clones.

Since the endometrial adenocarcinoma Ishikawa line exhibits characteristics of endometrial epithelia (Lessey, B. A., et al., 1996; Castelbaum, A. J., et al.; 1997; Gong, Y., et al., 1994), Ishikawa cells were used as a target in library screening.

Figure 1B:
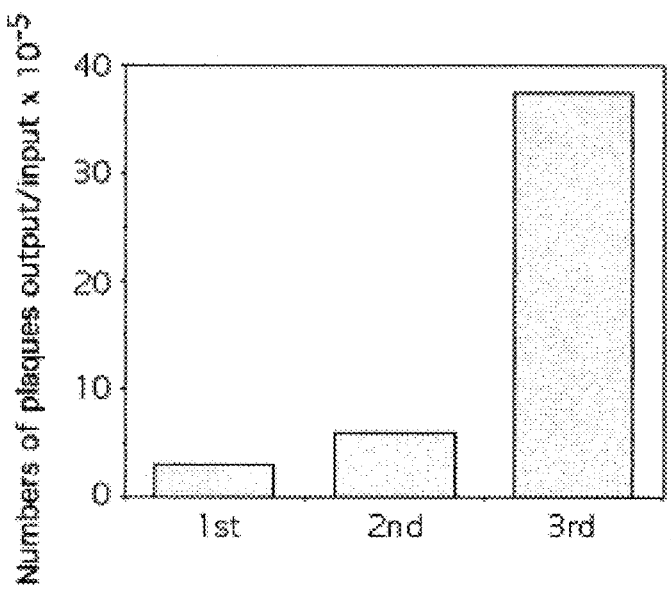

Because the goal was to identify a peptide that could be used to target peritoneal endometriosis, a subtraction step was included by mouse peritoneum during library screening (Stausbol-Gron, B., et al., 1996; Rasmussen, U. B., et al., 2002). Thus, a phage library ($10^{11}$ pfu) for linear 9-mer peptides was injected into the peritoneal cavity of a female mouse. The phage was incubated with peritoneal tissues by gentle massage. Thirty minutes later, the mouse was sacrificed and phage library was recovered from the peritoneum for the next step. This subtraction step was included in each cycle of the library screening (FIG. 1A). In order to identify a peptide that internalizes to the cytoplasm of endometrial glandular epithelial cells, so that a drug conjugated with the peptide could effectively kill endometrial cells, a phage library was screened by incubating it with Ishikawa cells at room temperature or at 37° C. to facilitate internalization of phage upon binding to the cell surface. After three rounds of library screening by this strategy, the number of phage that bound to Ishikawa cells relative to the total number of added phage increased 10,000-fold (FIG. 1B).

Figure 1C:
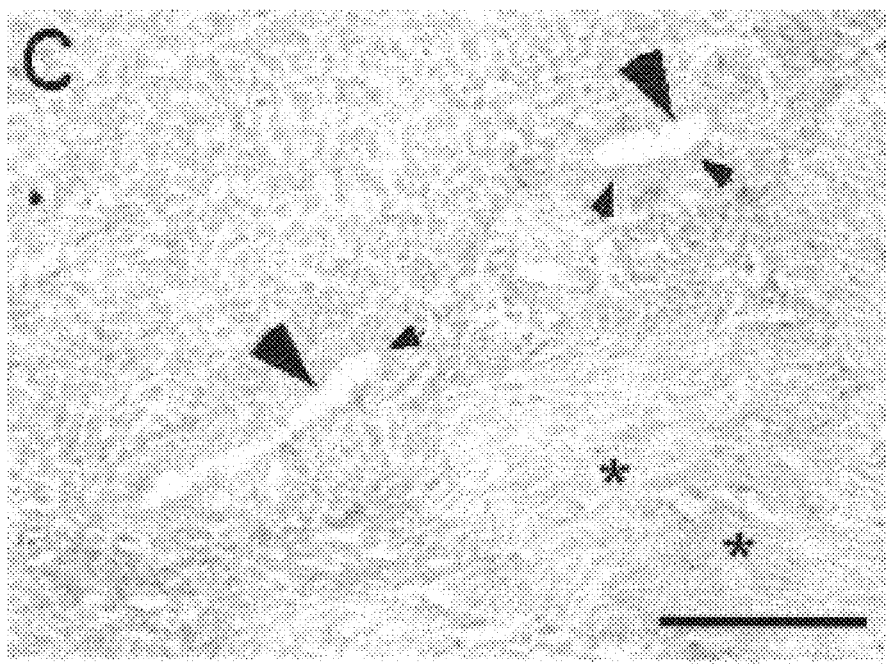
Figure 1D:
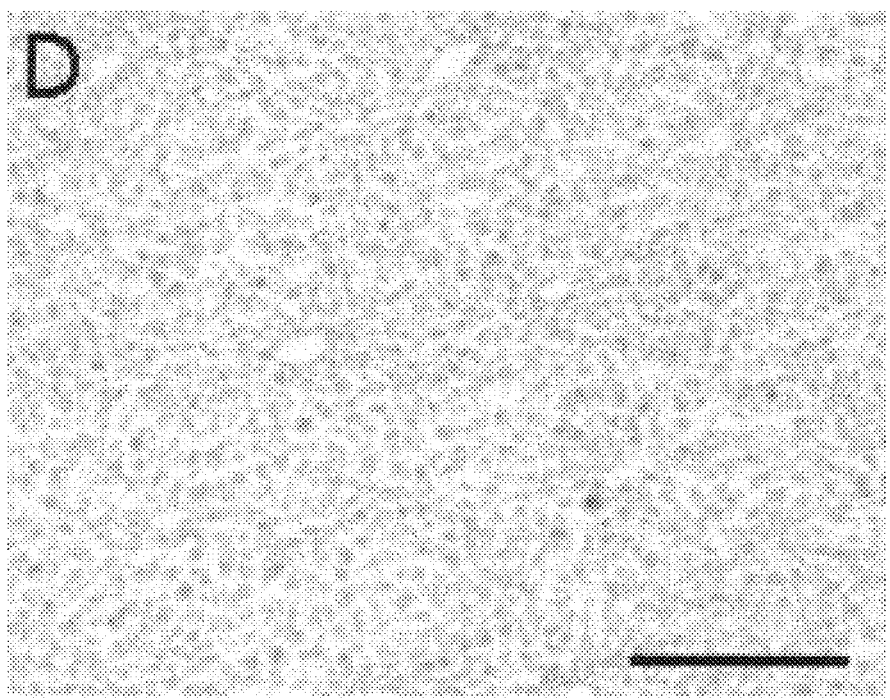

This phage pool was overlayed on frozen human tissue sections including uterine endometriosis, and the binding of phage to sections was visualized by the immunoperoxidase method using an anti-T7 phage antibody. Strong signals were detected at glandular epithelial cells particularly at apical cell surfaces in endometriosis (FIG. 1C), and relatively weak signals were seen in smooth muscle cells, blood vessels, or stromal cells in the same sections. There were no obvious signals for phage overlayed on sections from human lung, colon, heart, and liver (FIG. 1D). These results indicate that the phage pool contains a clone or clones specifically binding to endometrial glandular epithelial cells of endometriosis. Each phage clone in this pool was therefore sequenced to determine the peptide sequence displayed on the phage (Table I).

Binding Specificity of Cloned Phage.

Figure 2A:
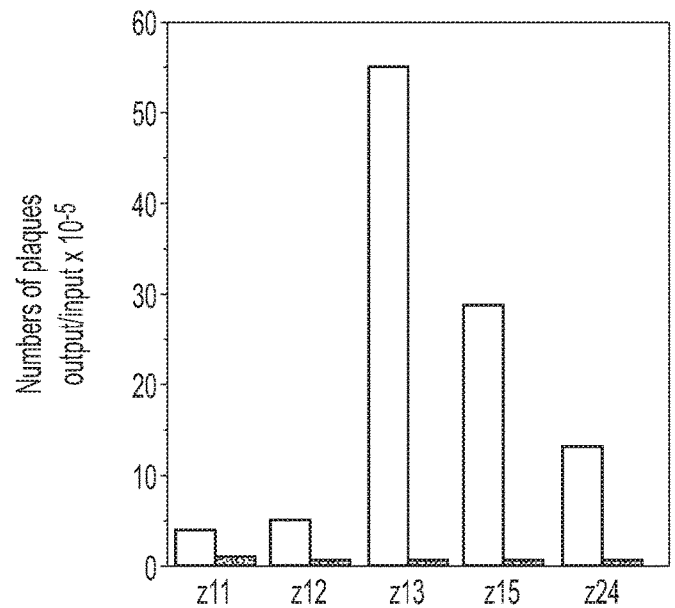
Figure 2B:
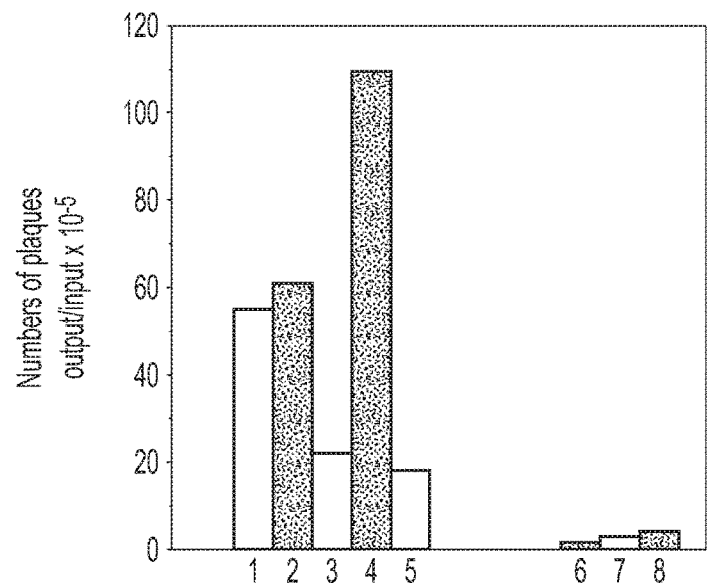

Several selected phage clones showed a consensus sequence (Table 3). Peptide sequences on z12, z13, and z15 clones were VRRA$\underline{X}$N$\underline{X}$PG (SEQ ID NO:1), where X represents a variable amino acid residue among these clones. When z12, z13, and z15 clones were individually overlayed on frozen endometrial sections, immunohistochemistry by anti-phage antibody showed a similar staining pattern to that shown in FIG. 1C. An in vitro binding assay of clones using Ishikawa cells and control A431 cells indicated that z12, z13, and z15 phage bind to Ishikawa cells at significantly higher efficiency than to A431 cells (FIG. 2A). The binding assay also showed that z13 is the strongest binder of the three to Ishikawa cells. In addition to Ishikawa cells, it was determined that z13 phage binds to endometrial adenocarcinoma, SNG-II, RL95-2, Hec1A, and HES cells, whereas it does not bind to A431, prostate cancer PC-3 and cervical cancer HeLa cells (FIG. 2B), indicating that its binding is specific to endometrial cells. These results led us to focus on z13 phage, which displays the peptide sequence VRRADNRPG (SEQ ID NO:3).

TABLE 3

Peptide sequences displayed by clone phage.

| clone name | peptide sequence | SEQ ID |
|---|---|---|
| z11 | VRSSRSTPG | SEQ ID NO: 7 |
| z12 | VRRANNPG | SEQ ID NO: 2 |
| z13 | VRRADNRPG | SEQ ID NO: 3 |
| z15 | VRRANNRPG | SEQ ID NO: 4 |
| z24 | MQRTRATPG | SEQ ID NO: 8 |

Consensus amino acid residues are shown by bold letters.

In Vitro Targeting Activity of Synthetic z13 Peptide.

When Ishikawa cells were overlayed with z13 phage and reacted with anti-phage antibody, immunofluorescence microscopy showed positive signals (FIG. 2C), whereas A431 cells overlayed with z13 phage did not show positive signals (FIG. 2D). FITC-z13, a synthetic fluorescence-tagged z13 peptide whose amino-terminus was conjugated, bound to Ishikawa cells (FIG. 2E), whereas FITC-z13 did not show fluorescence on A431 cells (FIG. 2F). These results indicate that peptide sequence displayed on z13 phage has binding activity to Ishikawa cells.

Z13 peptide was next chemically synthesized and conjugated at its amino terminus with palmitoyl C16 fatty acid, so that the peptide would be incorporated efficiently into liposomes. A fluorescent reagent (Qdot streptavidin) was enclosed in peptide-coated liposomes, enabling them to be traced under a fluorescence microscope. When z13 peptide-coated liposomes were added onto live Ishikawa cells, strong fluorescence signals were detected on the cell surface (FIG. 2G). By contrast, fluorescent liposomes coated with control (RGMSDTTAL, SEQ ID NO: 9) peptide, C16-m2, did not show fluorescence signals. These results indicate that liposomes coated with C16-z13 specifically target Ishikawa cells.

Synthetic cys-z13 peptide, CVRRADNRPG (SEQ ID NO:6), was conjugated to Qdot. When Qdot-cys-z13 was added to Ishikawa cell cultures, strong fluorescence was detected on Ishikawa cells (FIG. 2I), whereas Qdot-cys-m2, a Qdot conjugate of the control peptide, did not show fluorescence signals on Ishikawa cells (FIG. 2J). These results indicate that z13 peptide efficiently binds to Ishikawa cells regardless of its modification at the amino terminus.

In vivo targeting of endometriosis with synthetic z13 peptide. In vivo targeting activity of z13 phage was evaluated using an experimental endometriosis model in the SCID mouse. Human endometrial specimens transplanted to the peritoneal wall of SCID mice were prepared as described (Aoki, D., et al., 1994) (see experimental procedure above). Histology of implanted endometrial tissue demonstrated the presence of endometrial glandular tissue in a mixed background of stromal and inflammatory cells resembling lesions seen in endometriosis patients. Qdot-z13 was injected into the peritoneum of the endometriosis model mouse. Thirty minutes later, mice were sacrificed, and endometrial lesions as well as tissues facing the peritoneal cavity were isolated. Fluorescence microscopy of tissue sections demonstrated a clear fluorescence signal at the surface epithelia of endometriosis lesions (FIG. 3A). Occasionally, strong fluorescence was detected on the surface of the mouse peritoneum without recognizable endometriosis (FIG. 3B). Although relatively infrequent, fluorescence was detected on the surface of the mouse uterus, ovary, and oviduct (FIG. 3C). Fluorescence was not detected on the surface of the liver (FIG. 3D). Control Qdot-cys-m2 injected into the endometriosis mouse model did not show fluorescence in endometriosis lesions (FIG. 3E) or in other mouse tissues facing the peritoneum (FIG. 3F,G,H). When Qdot-cys-z13 was injected to SCID mouse without human endometriosis, no fluorescence signal was detected into the mouse tissues facing the peritoneal cavity.

Identification of Human Endometrial Cells on the Mouse Peritoneum.

The patterns of Qdot-cys-z13 binding (FIG. 3) indicated that human endometrial cells spread through the peritoneal cavity and grew at various locations. Immunocytochemistry using rabbit antibody specific to human PR (Traish, A. M. & Wotiz, H. H., 1990) showed strong nuclear staining of human endometrial stromal cells and glandular epithelial cells in the transplant (FIG. 4A). The cytoplasm of these cells was also stained by this antibody. When this antibody was reacted with specimens from control mice without endometrial transplants, the antibody stained mouse uterus and oviduct cells, suggesting the cross-immunoreactivity of the antibody to mouse PR. By contrast, peritoneal cells from control mice were not stained with this antibody (FIG. 4B).

Although the peritoneum of mice receiving human endometrial transplants was largely negative for PR, positive staining was found in the cytoplasm of cells in the outer layers of the peritoneum (FIG. 4C) and in nuclei in the peritoneum (FIG. 4D). Because this antibody did not react with peritoneal cells in control mice (FIG. 4B), these results indicate that immunoreactive cells (FIG. 4C,D) originate from the human endometrial transplant. When immunohistochemistry was undertaken in the endometriosis model mouse injected with Qdot-cys-z13, red Qdot-cys-z13 signals and green PR signals often overlapped (FIG. 4E,F). These results indicate that Qdot-cys-z13 targeted to human endometrial cells attached to the peritoneum in vivo in the mouse.

2. Example 2

Liposomes were made that included C16 fatty acid-conjugated z13 peptides, the apoptosis-inducing glycolipid, GD3 (De Maria, R, 1997; Malisan, F., 2002), or both. GD3 is a natural and widely expressed glycosphingolipid. GD3 localizes in the plasma membranes. However, when GD3 is localizes to the cytoplasm, GD3 binds to the mitochondrial membranes and induces apoptosis. When liposomes containing only GD3 were added to human endometrial Ishikawa cells, the cells were killed by apoptosis, albeit inefficiently. However, when liposomes containing both z13 and GD3 were added to Ishikawa cells, the cells were not killed. These result indicate that the receptor for z13 peptide is a membrane protein of sorting pathway, i.e., the receptor bound z13/GD3 liposomes, internalized to endosomes, then circulated back to the cell surface. Therefore GD3 in the z13 containing liposomes were not delivered to the cytoplasm of the target cells. Inclusion of internalization sequences in liposomes and/or on the targeting peptide can aid in internalization of the targeting peptide and material in the composition comprising the targeting peptide. For example, liposomes containing C16 fatty acid-conjugated TAT peptide, C16 fatty acid-conjugated z13 peptide, and GD3 can be applied to endometrial cells to evaluate internalization. This can allow GD3 internalization to the cytoplasm of targeted cells, and induction of apoptosis.

B. References

Aoki, D., Katsuki, Y., Shimizu, A., Kakinuma, C. & Nozawa, S. (1994) Obstet Gynecol 83, 220-8.

Arap, W., Pasqualini, R. & Ruoslahti, E. (1998) Science 279, 377-80.

Arici, A., Matalliotakis, I., Goumenou, A., Koumantakis, G., Fragouli, Y. & Mahutte, N. G. (2003) Am J Reprod Immunol 49, 70-4.

Arimoto, T., Katagiri, T., Oda, K., Tsunoda, T., Yasugi, T., Osuga, Y., Yoshikawa, H., Nishii, O., Yano, T., Taketani, Y. & Nakamura, Y. (2003) Int J Oncol 22, 551-60.

Awwad, J. T., Sayegh, R. A., Tao, X. J., Hassan, T., Awwad, S. T. & Isaacson, K. (1999) Hum Reprod 14, 3107-11.

Barbieri, R. L. & Missmer, S. (2002) Ann N Y Acad Sci 955, 23-33; discussion 34-6, 396-406.

Barbieri, R. L. (1988) N Engl J Med 318, 512-4.

Castelbaum, A. J., Ying, L., Somkuti, S. G., Sun, J., Ilesanmi, A. O. & Lessey, B. A. (1997) J Clin Endocrinol Metab 82, 136-42.

Cramer, D. W. & Missmer, S. A. (2002) Ann N Y Acad Sci 955, 11-22; discussion 34-6, 396-406.

De Maria, R., Lenti, L., Malisan, F., d'Agostino, F., Tomassini, B., Zeuner, A., Rippo, M. R., and Testi, R. Requirement for GD3 ganglioside in CD95- and ceramide-induced apoptosis. Science, 277: 1652-1655, 1997.

Desai, N. N., Kennard, E. A., Kniss, D. A. & Friedman, C. I. (1994) Fertil Steril 61, 760-6.

Ellerby, H. M., Arap, W., Ellerby, L. M., Kain, R., Andrusiak, R., Rio, G. D., Krajewski, S., Lombardo, C. R., Rao, R., Ruoslahti, E., Bredesen, D. E. & Pasqualini, R. (1999) Nat Med 5, 1032-8.

Essler, M. & Ruoslahti, E. (2002) Proc Natl Acad Sci USA 99, 2252-7.

Eyster, K. M., Boles, A. L., Brannian, J. D. & Hansen, K. A. (2002) Fertil Steril 77, 38-42.

Fukuda, M. N., Sato, T., Nakayama, J., Klier, G., Mikami, M., Aoki, D. & Nozawa, S. (1995) Genes Dev 9, 1199-210.

Gerlag, D. M., Borges, E., Tak, P. P., Ellerby, H. M., Bredesen, D. E., Pasqualini, R., Ruoslahti, E. & Firestein, G. S. (2001) Arthritis Res 3, 357-61.

Gong, Y., Murphy, L. C. & Murphy, L. J. (1994) J Steroid Biochem Mol Biol 50, 13-9.

Grummer, R., Schwarzer, F., Bainczyk, K., Hess-Stumpp, H., Regidor, P. A., Schindler, A. E. & Winterhager, E. (2001) Hum Reprod 16, 1736-43.

Haffner, M. E., Whitley, J. & Moses, M. (2002) Nat Rev Drug Discov 1, 821-5.

Hoffman, J. A., Laakkonen, P., Porkka, K. & Ruoslahti, E. (2002) Phage Display: A practical Approach Clarkson, T., and Lowman, H., eds. Oxford University Press.

Kao, L. C., Germeyer, A., Tulac, S., Lobo, S., Yang, J. P., Taylor, R. N., Osteen, K., Lessey, B. A. & Giudice, L. C. (2003) Endocrinology 144, 2870-81.

Kolonin, M. G., Saha, P. K., Chan, L., Pasqualini, R. & Arap, W. (2004) Nat Med 10, 625-32.

Lessey, B. A., Damjanovich, L., Coutifaris, C., Castelbaum, A., Albelda, S. M. & Buck, C. A. (1992) J. Clin. Invest. 90, 188-195.

Lessey, B. A., Ilesanmi, A. O., Castelbaum, A. J., Yuan, L., Somkuti, S. G., Chwalisz, K. & Satyaswaroop, P. G. (1996) J Steroid Biochem Mol Biol 59, 31-9.

Malisan, F. and Testi, R. GD3 ganglioside and apoptosis. Biochim Biophys Acta, 1585: 179-187, 2002.

Matsuzaki, S., Canis, M., Vaurs-Barriere, C., Pouly, J. L., Boespflug-Tanguy, O., Penault-Llorca, F., Dechelotte, P., Dastugue, B., Okamura, K. & Mage, G. (2004) Mol Hum Reprod 10, 719-28.

Murphy, A. A. (2002) Ann N Y Acad Sci 955, 1-10; discussion 34-6, 396-406.

Nozawa, S., Sakayori, M., Ohta, K., Iizuka, R., Mochizuki, H., Soma, M., Fujimoto, J., Hata, J., Iwamori, M. & Nagai, Y. (1989) Am J Obstet Gynecol 161, 1079-86.

Oku, N., Asai, T., Watanabe, K., Kuromi, K., Nagatsuka, M., Kurohane, K., Kikkawa, H., Ogino, K., Tanaka, M., Ishikawa, D., Tsukada, H., Momose, M., Nakayama, J. & Taki, T. (2002) Oncogene 21, 2662-9.

Pasqualini, R. & Ruoslahti, E. (1996) Nature 380, 364-6.

Pasqualini, R., Koivunen, E., Kain, R., Landenranta, J., Sakamoto, M., Stryhn, A., Ashmun, R. A., Shapiro, L. H., Arap, W. & Ruoslahti, E. (2000) Cancer Res 60, 722-7.

Rajotte, D. & Ruoslahti, E. (1999) J. Biol. Chem. 274, 11593-11598.

Rajotte, D., Arap, W., Hagedorn, M., Koivunen, E., Pasqualini, R. & Ruoslahti, E. (1998) J Clin Invest 102, 430-437.

Rasmussen, U. B., Schreiber, V., Schultz, H., Mischler, F. & Schughart, K. (2002) Cancer Gene Ther 9, 606-12.

Ruoslahti, E. (2000) Semin Cancer Biol 10, 435-42.

Ruoslahti, E. (2002) Drug Discov Today 7, 1138-43.

Smith, G. P. (1985) Science 228, 1315-7.

Stausbol-Gron, B., Wind, T., Kjaer, S., Kahns, L., Hansen, N. J., Kristensen, P. & Clark, B. F. (1996) FEBS Lett 391, 71-5.

Thomas, E. J. & Campbell, I. G. (2000) Gynecol Obstet Invest 50 Suppl 1, 2-10.

Torchilin, V. P., Rammohan, R., Weissig, V., and Levchenko, T. S. TAT peptide on the surface of liposomes affords their efficient intracellular delivery even at low temperature and in the presence of metabolic inhibitors. Proc Natl Acad Sci USA, 98: 8786-8791, 2001.

Traish, A. M. & Wotiz, H. H. (1990) Endocrinology 127, 1167-75.

Vigano, P., Gaffuri, B., Somigliana, E., Busacca, M., Di Blasio, A. M. & Vignali, M. (1998) Mol Hum Reprod 4, 1150-6.

C. Sequences

| Sequence | |
|---|---|
| VRRAXNXPG (X can be any amino acid) | SEQ ID NO: 1 |
| VRRANNLPG | SEQ ID NO: 2 |
| VRRADNRPG | SEQ ID NO: 3 |
| VRRANNRPG | SEQ ID NO: 4 |
| CRGMSDTTAL | SEQ ID NO: 5 |
| CVRRADNRPG | SEQ ID NO: 6 |
| VRSSRSTPQ | SEQ ID NO: 7 |
| MQRTRATPG | SEQ ID NO: 8 |
| RGMSDTTAL | SEQ ID NO: 9 |
| RQPKIWFPNRRKPWKK | SEQ ID NO: 10 |
| GRKKRRQRPPQ | SEQ ID NO: 11 |
| RQIKIWFQNRRMKWKK | SEQ ID NO: 12 |
| RQIAIWFQNRRMKWAA | SEQ ID NO: 13 |
| RKKRRQRRR | SEQ ID NO: 14 |
| TRSSRAGLQFPVGRVHRLLRK | SEQ ID NO: 15 |
| GWTLNSAGYLLGKINKALAALAKKIL | SEQ ID NO: 16 |
| KLALKLALKALKAALKLA | SEQ ID NO: 17 |
| AAVALLPAVLLALLAP | SEQ ID NO: 18 |
| VPMLK-PMLKE | SEQ ID NO: 19 |
| MANLGYWLLALFVTMWTDVGLCKKRPKP | SEQ ID NO: 20 |
| LLIILRRRIRKQAHAHSK | SEQ ID NO: 21 |
| KETWWETWWTEWSQPKKKRKV | SEQ ID NO: 22 |
| RGGRLSYSRRRFSTSTGR | SEQ ID NO: 23 |
| SDLWEMMMVSLACQY | SEQ ID NO: 24 |
| TSPLNIHNGQK | SEQ ID NO: 25 |

We claim:

1. A composition comprising a targeting peptide that selectively binds an endometriosis cell, wherein the targeting peptide comprises at least 9 amino acids, wherein the targeting peptide has at least 70% sequence identity with SEQ ID NO:3, wherein any variation from SEQ ID NO:3 is a conservative amino acid substitution, and wherein the targeting peptide is 50 amino acids in length or less.

2. The composition of claim 1, wherein the targeting peptide comprises the amino acid sequence set forth in SEQ ID NO:3.

3. The composition of claim 1, wherein the targeting peptide has at least 80% sequence identity to the amino acid sequence set forth in SEQ ID NO:3.

4. The composition of claim 3, wherein the targeting peptide has at least 85% sequence identity to the amino acid sequence set forth in SEQ ID NO:3.

5. The composition of claim 4, wherein the targeting peptide has at least 90% sequence identity to the amino acid sequence set forth in SEQ ID NO:3.

6. The composition of claim 1, wherein the targeting peptide comprises an amino acid segment having at least 85% sequence identity to the amino acid sequence set forth in SEQ ID NO:3.

7. The composition of claim 1, further comprising a known effector molecule.

8. The composition of claim 7, wherein the effector molecule is a small molecule, pharmaceutical drug, toxin, fatty acid, detectable marker, conjugating tag, nanoshell, or enzyme.

9. The composition of claim 7, wherein the effector molecule is covalently linked to the targeting peptide.

10. The composition of claim 9, wherein the effector molecule is linked to the amino terminal end of the targeting peptide.

11. The composition of claim 9, wherein the effector molecule is linked to the carboxy terminal end of the targeting peptide.

12. The composition of claim 9, wherein the effector molecule is linked to an amino acid within the targeting peptide.

13. The composition of claim 7, further comprising a linker connecting the effector molecule and targeting peptide.

14. The composition of claim 1, further comprising a progestational agent.

15. The composition of claim 1, further comprising a Gonadotropin-releasing hormone (GnRH), GnRH analog, or GnRH agonist.

16. The composition of claim 1, further comprising an aromatase inhibitor.

17. The composition of claim 1, further comprising a narcotic.

18. The composition of claim 1, further comprising a non-steroidal anti-inflammatory drug (NSAID).

19. The composition of claim 1, further comprising a pharmaceutically acceptable carrier.

20. A method comprising administering to a subject a composition comprising the composition of claim 1, wherein the subject has or can have endometriosis, endometriosis cells, or both, wherein the composition further comprises an effector molecule, wherein the effector molecule is a detectable marker, a small molecule or pharmaceutical drug, or both.

21. The method of claim 20, wherein the subject comprises a cell, wherein the cell is an endometriosis cell.

22. A method of detecting endometriosis in a subject, the method comprising administering to the subject the composition of claim 1 and detecting the composition in the subject, thereby detecting endometriosis, wherein the subject has or can have endometriosis, wherein the composition further comprises an effector molecule, wherein the effector molecule is a detectable marker.

23. A method of diagnosing endometriosis in a subject, the method comprising administering to the subject the composition of claim 1 and detecting the composition in the subject, thereby diagnosing endometriosis in the subject, wherein the subject has or can have endometriosis, wherein the composition further comprises an effector molecule, wherein the effector molecule is a detectable marker.

24. A method of determining the prognosis of endometriosis in a subject, the method comprising administering to the subject the composition of claim 1 and detecting the composition in the subject, wherein the level, amount, concentration, or a combination of binding of the composition to endometriosis tissue in the subject indicates the prognosis of the endometriosis in the subject, wherein the subject has endometriosis, wherein the composition further comprises an effector molecule, wherein the effector molecule is a detectable marker.

25. A method of determining the progress of endometriosis in a subject, the method comprising administering to the subject the composition of claim 1, detecting the composition in the subject, and repeating the administration and detection at a later time, wherein a change in the level, amount, concentration, or a combination of binding of the composition to endometriosis tissue in the subject indicates the progress of the endometriosis in the subject, wherein the subject has endometriosis, wherein the composition further comprises an effector molecule, wherein the effector molecule is a detectable marker.

26. A method of determining the progress treatment of endometriosis in a subject, the method comprising administering to the subject the composition of claim 1, detecting the composition in the subject, and repeating the administration and detection following treatment, wherein a change in the level, amount, concentration, or a combination of binding of the composition to endometriosis tissue in the subject indicates the progress the treatment of the endometriosis in the subject, wherein the subject has endometriosis, wherein the composition further comprises an effector molecule, wherein the effector molecule is a detectable marker.

27. The composition of claim 1, wherein the targeting peptide comprises the amino acid sequence set forth in SEQ ID NO:3.

28. The composition of claim 1, wherein the targeting peptide has at least 89% sequence identity to the amino acid sequence set forth in SEQ ID NO:3.

29. The composition of claim 1, wherein the amino acid at position 5 is asparagine or a conservative variant thereof, or aspartic acid or a conservative variant thereof, wherein the amino acid at position 7 is leucine or a conservative variant thereof, or arginine or a conservative variant thereof.

30. The composition of claim 1, wherein the amino acid at position 5 is asparagine, aspartic acid, glutamine, glutamic acid, or histidine, wherein the amino acid at position 7 is leucine, arginine, isoleucine, valine, lysine, or glutamine.

31. The composition of claim 1, wherein the amino acids at position 5 and 7, respectively, are asparagine and arginine or aspartic acid and leucine.

* * * * *